United States Patent [19]

O'Rourke

[11] Patent Number: 5,265,011
[45] Date of Patent: Nov. 23, 1993

[54] METHOD FOR ASCERTAINING THE PRESSURE PULSE AND RELATED PARAMETERS IN THE ASCENDING AORTA FROM THE CONTOUR OF THE PRESSURE PULSE IN THE PERIPHERAL ARTERIES

[75] Inventor: Michael F. O'Rourke, Hunters Hill, Australia

[73] Assignee: Eastern Medical Testing Services, Inc., Quincy, Mass.

[21] Appl. No.: 790,644

[22] Filed: Nov. 8, 1991

Related U.S. Application Data

[63] Continuation-in-part of Ser. No. 497,483, Mar. 22, 1990, abandoned, which is a continuation-in-part of Ser. No. 464,890, Jan. 16, 1990, abandoned, which is a continuation-in-part of Ser. No. 328,285, Mar. 24, 1989, abandoned.

[51] Int. Cl.$^5$ .......................... G06F 15/42; A61B 5/02
[52] U.S. Cl. ................................ 364/413.03; 128/672
[58] Field of Search ............................. 128/672, 680; 364/413.01, 413.02, 413.03, 413.05

[56] References Cited

PUBLICATIONS

Kelly et al., "Noninvasive determination of age-related changes in the human arterial pulse", *St. Vincent's Hospital*, Sydney, Australia, 80 (6), Dec. 1989, pp. 1652-1659 (abstract only).

Lasance et al., "Peripheral pulse contour analysis in determining stroke volume", *PROG. REP. MED. FYS. INST. TNO* (Netherlands), No. 4, 1976, pp. 59-62.

Kelly et al., "Nitrogylcerin has more favorable effects on left ventricular afterload than apparent from measurement of pressure in a peripheral artery", *EUR. HEART J.*, 11(2), 1990, pp. 138-144 (abstract only).

Simkus et al., "Radial arterial pressure measurements may be a poor guide to the beneficial effects of nitroprusside on left ventricular systolic pressure in congestive heart failure", *AM. J. CARDIOL.*, 66(3), 1990, pp 323-326 (abstract only).

Waldman, "Modeling of the coupling of the left ventricle to the peripheral circulation" *Ventricular/Vascular Coupling:Clinical, Physiological, and Engineering Aspects*, Springer Verlag Inc., 1987, pp. 301-333 (abstract only).

O'Rourke, "Systolic blood pressure:arterial compliance and early wave reflection, and their modification by antihypertensive therapy", *J HUM. HYPERTENS.* (UNITED KINGDOM), 1989 pp. 47-52 (abstract only).

Szucs, "Approximate Identification of the Aortic Pressure Transfer", *IFAC Theory and Application of Digital Control*, New Delhi, India, 1982, pp. 393-394.

*Primary Examiner*—Robert A. Weinhardt
*Assistant Examiner*—David Huntley
*Attorney, Agent, or Firm*—Cesari and McKenna

[57] ABSTRACT

The system measures the pressure pulses in an upper body peripheral artery and produces an electrical signal which represents the contours of these pulses. It then digitizes the signal and synthesizes the pressure pulses in the ascending aorta using either a frequency-domain or a time-domain calculation method. Next, the system separately averages the signals corresponding to the measured pulses and those corresponding to the synthesized pulses, and forms for each an "average pulse." The system identifies the wave foot in each of the average pulses, identifies the incisura in the average peripheral pulse, determines the amount of time associated with systole and, based on this time, segments the synthesized pulse into systolic and diastolic components. The system then identifies the two pressure peaks and determines their amplitudes using either the average peripheral pulse or the average synthesized pulse, by taking first and third derivatives of the pulses and determining the locations of the relevant minimum and maximum points. The system then determines the peak and mean pressures throughout the wave and at various critical points such as the primary pressure peak, the reflective wave peak, and throughout systole and diastole. Using these peaks and pressures, the system calculates maximum and mean systolic and diastolic pressures, an augmentation index, a measure of subendocardial viability, and the pressure at the end of systole.

25 Claims, 25 Drawing Sheets

TRANSFER FUNCTION PROCESSOR ~58

INDIVIDUAL TRANSFER FUNCTIONS

$$H(w)^*_{AA-BA} = \frac{BA(w)}{AA(w)}$$

$$H(w)^*_{AA-RA} = \frac{RA(w)}{AA(w)}$$

$$H(w)^*_{AA-CA} = \frac{CA(w)}{AA(w)}$$

GROUPED AND SMOOTHED TRANSFER FUNCTIONS

$$H(w)_{AA-BA} = \frac{BA(w)}{AA(w)}$$

$$H(w)_{AA-RA} = \frac{RA(w)}{AA(w)}$$

$$H(w)_{AA-CA} = \frac{CA(w)}{AA(w)}$$

FROM MEASURING DEVICE: $AA(t), BA(t), RA(t), CA(t)$ → FOURIER TRANSFORM → $AA(w), BA(w), RA(w), CA(w)$

FIG. 5

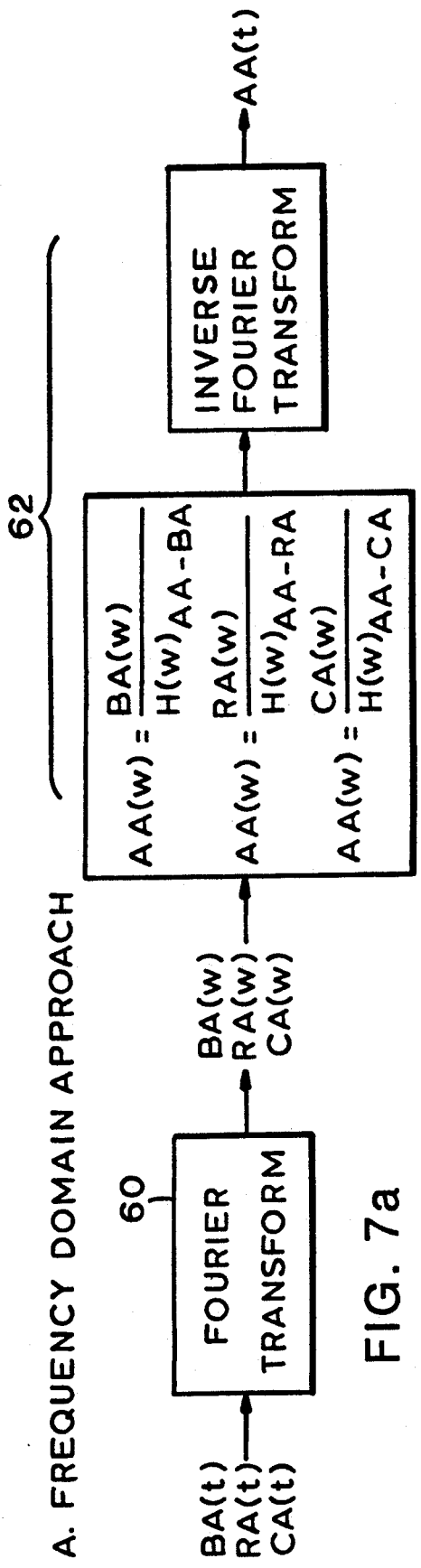
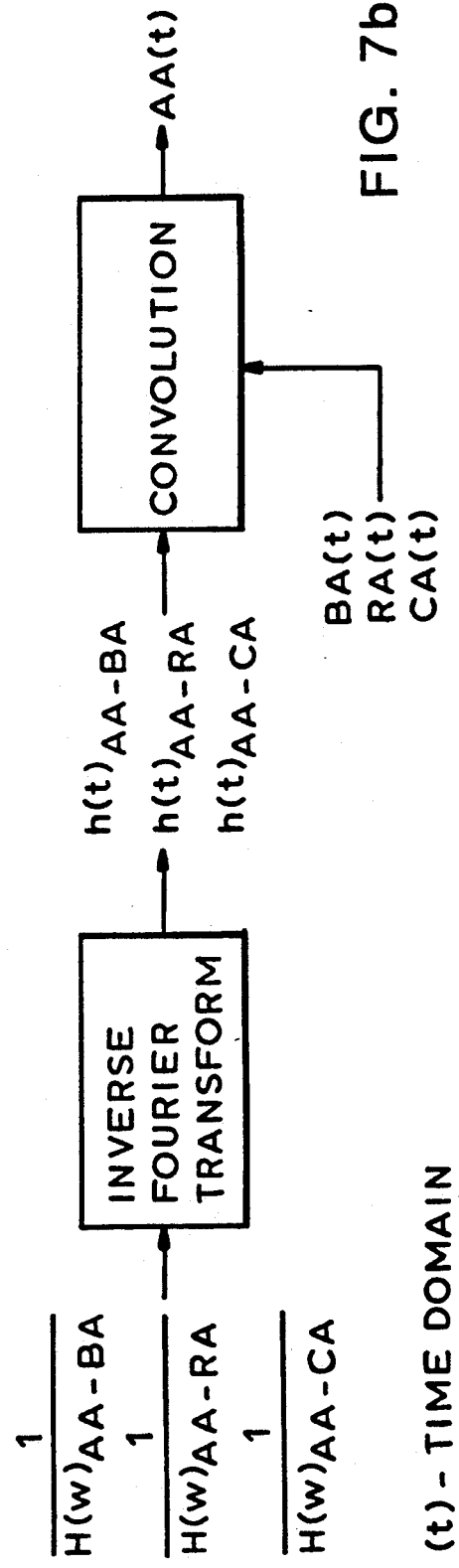
FIG. 7a — A. FREQUENCY DOMAIN APPROACH
FIG. 7b — B. TIME DOMAIN APPROACH
(t) – TIME DOMAIN
(w) – FREQUENCY DOMAIN
H IS TRANSFER FUNCTION METHOD FOR ASCERTAINING THE PRESSURE PULSE AND RELATED PARAMETERS IN THE ASCENDING AORTA FROM THE CONTOUR OF THE PRESSURE PULSE IN THE PERIPHERAL ARTERIES This application is a continuation-in-part of the application Ser. No. 07/497,483, now abandoned, filed Mar. 22, 1990, which is a continuation in part of the application Ser. No. 07/464,890 filed Jan. 16, 1990, now abandoned which is a continuation in part of the application Ser. No. 07/328,285 filed Mar. 24, 1989, now abandoned.

BACKGROUND

The contour of the central arterial blood pressure pulse of an adult is different from the contour of the pressure pulse of a youth. The pressure pulse of an adult has an augmented peak in late systole, and a near-exponential decay during diastole, while the pressure pulse of a youth has a rounded peak throughout systole and a second peak during diastole.

The differences in the two pressure pulse patterns are attributable largely to an early return in an adult of a secondary reflection wave, that is, a reflection of the primary pressure pulse along the arterial tree from the periphery in the lower part of the body. The early return of the secondary wave is due to an increase in the velocity of the arterial pulse caused by a stiffening and/or mismatch of the conduit arteries in the adult. Because of its early return, the secondary wave arrives at the heart during its contraction, and thus augments the systolic peak of the pressure pulse in the left ventricle of the heart, in the ascending aorta and in other proximal arteries.

A youth has arteries which are more distensible, and therefore, the arterial pulse wave is slower in the youth than in the adult. Thus the secondary wave from the lower body does not return as early in the pulse cycle, and therefore, it does not combine with, or augment, the systolic peak of the central pressure pulse. Instead, the pulse has a second peak in diastole which corresponds to the later return of the secondary wave.

With increasing age, characteristic changes can be seen in the contour and amplitude of the pressure pulse in both the central and the peripheral arteries, due largely to the earlier return of the secondary (reflected) wave from the lower body. From the fourth decade on, a relatively large augmentation of the pulses in late systole can be observed in the carotid and ascending aorta, and left ventricle. Such augmentation is not observed, or not observed to the same degree, in the pulses in the peripheral arteries of the upper limb, however, until the eighth decade. Thus, measurements of blood pressure in the peripheral arteries of the upper limb are not completely accurate representations of the pressure in the carotid artery or ascending aorta.

The discrepancies in pressure between central and peripheral arteries help to explain why, in arterial hypertension, the degree of arterial damage and the severity of left ventricular hypertrophy do not always correlate well with the level of brachial systolic pressure. The discrepancies also explain why regression of left ventricular hypertrophy induced by various drugs does not always accord with the degree of reduction in brachial arterial pressure.

The usual clinically-accepted method for determination of the hydraulic load presented to the left ventricle in man is through measurement of systolic arterial pressure in the brachial artery with a sphygmomanometer. The clinician then uses the measured systolic pressure as an indication of the maximum pressure in all major arteries of the body and in the left ventricle of the heart. Such an assumption is not justified, however, because of the differences in the effect of wave reflection in the periphery of the body and the central arteries, as discussed above.

While these problems with blood pressure interpretation are generally known, no one has previously developed a noninvasive measurement method which is more accurate than the sphygmomanometer for assessment of central aortic pressure, or of left ventricular pressure during systole. Yet it is highly desirable to be able to ascertain augmentation of pressure pulses in the ascending aorta from an analysis of the contour of the primary and secondary pressure waves in peripheral arteries. This would allow physicians to diagnose and treat more appropriately abnormal blood pressure and arterial conditions early in life, and thus, aid the physicians in pre-empting the dangerous effects of such conditions in later life. It would also assist in treating established disease including cardiac failure, angina pectoris and hypertension, and for investigating left ventricular function.

SUMMARY OF THE INVENTION

The invention is a method for calculating from the contours of the pressure pulses recorded invasively or noninvasively in the brachial and/or radial arteries (i) the contour of the pressure pulses in the ascending aorta, (ii) the mean diastolic and mean systolic pressure in the ascending aorta and related indices, (iii) the absolute systolic pressure in the ascending aorta (iv) the absolute systolic pressure in the left ventricle and (v) the degree of systolic pressure augmentation.

The pressure in the ascending aorta is related to a combination of the primary pressure pulse and the secondary pressure wave, which is a reflection of the primary pressure pulse returning from the periphery of the lower part of the body. Measurement of the pressure at the peripheral arteries does not alone provide accurate figures for the maximum systolic or diastolic pressure in the central arteries, for example, in the ascending aorta, nor of maximum pressure in the left ventricle of the heart. Analysis of the contour of the pressure wave in the peripheral arteries and the contour of the synthesized ascending aortic pressure pulses can provide indirect measurement of the maximum systolic and diastolic pressure in the central arteries and maximum pressure in the left ventricle. In particular, the maximum central arterial pressure and maximum left ventricular pressure can be determined from an analysis of the contour of the peripheral and synthesized pressure pulses and the relationship between pulse peaks which relate to the maximum primary pressure and the maximum secondary wave pressure, respectively.

The positions, and thus the amplitudes, of the two peaks are not always readily apparent from a visual inspection of the pulse contours, particularly when the secondary wave returns early in systole. The inventive system first determines the positions of these two peaks, and the positions of the wave foot and the incisura, which indicate the beginning and end of systole, respectively, and then analyses their positions and their amplitudes to ascertain the maximum systolic pressure in the ascending aorta and left ventricle, the mean systolic and mean diastolic pressures in the ascending aorta and the degree of augmentation caused by early wave reflection.

In brief summary, the inventive system measures the pressure pulses in a peripheral artery either noninvasively using a tonometer or other device or invasively using a conventional intra-arterial device. Either method of measurement produces an electrical signal representative of the contours of the pressure pulses. The system then digitizes the signal and synthesizes the pressure pulses in the ascending aorta using either a frequency-domain calculation method or a time-domain calculation method. Next, the system separately averages the signals corresponding to the measured pulses and the signals corresponding to the synthesized pulses, and forms for each an "average pulse." The system then identifies the wave foot and incisura in the averaged peripheral pulse, determines the amount of time associated with systole and, based on this time and the identification of the ascending aortic wave foot, segments the synthesized pulse into systolic and diastolic components. The system then identifies the two pressure peaks and determines their amplitudes using either the averaged peripheral pulse or the averaged synthesized pulse, by taking various derivatives of the pulses as set forth in the detailed description.

The system can then accurately determine the peak and mean pressures throughout the wave and at various critical points such as the primary pressure peak, the reflective wave peak, and throughout systole and diastole. Once the system has determined these peak and mean pressures, it calculates various indices from which a doctor can diagnose, treat and monitor assorted heart and vascular conditions. Before the inventive system, such indices could only be calculated from measurements taken invasively in the aorta.

BRIEF DESCRIPTION OF THE DRAWINGS

This invention is pointed out with particularity in the appended claims. The above and further advantages of this invention may be better understood by referring to the following description taken in conjunction with the accompanying drawings, in which:

FIG. 5 depicts in block diagram form a transfer function processor;

FIGS. 7a and 7b depicts in block diagram form processors for synthesizing from a measured peripheral pressure wave an ascending aorta pressure wave;

DETAILED DESCRIPTION

1. Pressure Measurements

Figure 1:
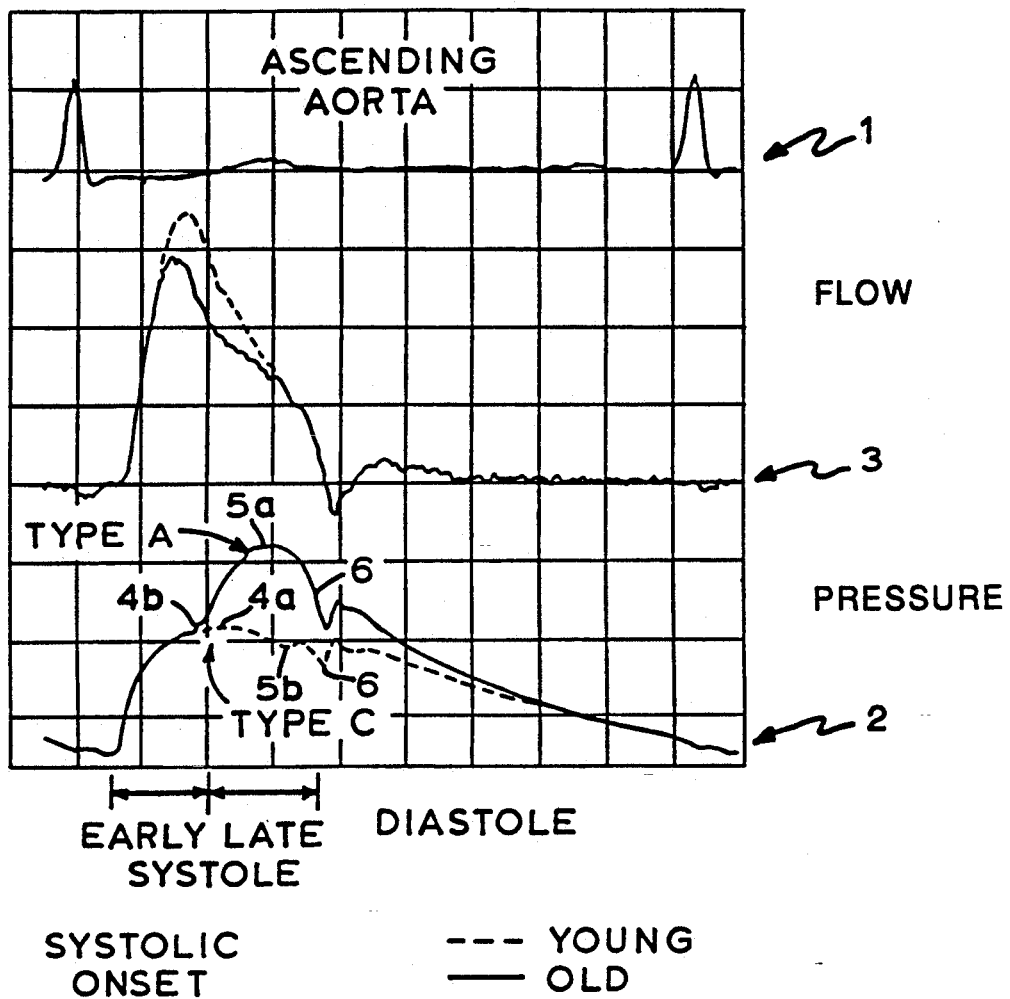
FIG. 1 is a diagram of the blood flow (above) and pressure (below) pulses in the ascending aorta, which depicts pressure pulses for both young and old persons.

FIG. 1 illustrates, for a heart blood pumping cycle, ascending aortic pressure and blood flow velocity in a relatively young person (type B or C, dotted lines) and an older person (type A, solid lines). Curve 1 represents an EKG reading of a number of heart blood pumping cycles. Curves 2 and 3 represent aortic pressure and blood flow velocity, respectively, during the systolic and diastolic portions of one pumping cycle.

The dotted-line portion of curve 2, which corresponds to an aortic pressure pulse of a youth, illustrates a non-augmented pressure pulse. The pulse has a maximum peak 4c in early systole, a smaller secondary wave peak 5c in late systole, a dicrotic notch, or incisura 6 at the onset of diastole, and a gradual decay during diastole. The blood flow associated with this non-augmented pressure wave is shown by the dotted-line portion of curve 3. Accordingly, blood flow velocity is at a relative maximum when the associated pressure wave is non-augmented.

The solid-line portion of curve 2, which corresponds to an aortic pressure pulse of an older subject, illustrates an augmented pressure pulse. The pulse has a peak 4a in early systole, an augmented secondary wave peak 5a in late systole, a dicrotic notch 6 at the onset of diastole and near exponential decay during diastole. The corresponding blood flow velocity is shown by the solid-line portion of curve 2. The blood flow in an older subject is seen to be slower than in a youth, while the aortic pressure required to force the blood to flow in the older subject is greater.

Left ventricular pressure is not shown in this figure. During systole (i.e. from the foot of the pressure wave to the incisura) left ventricular pressure is identical to ascending aortic pressure and shows the same late systolic augmentation as aortic pressure. Accordingly, the discussion of ascending aortic pressure during systole also applies to left ventricular pressure.

Figure 2:
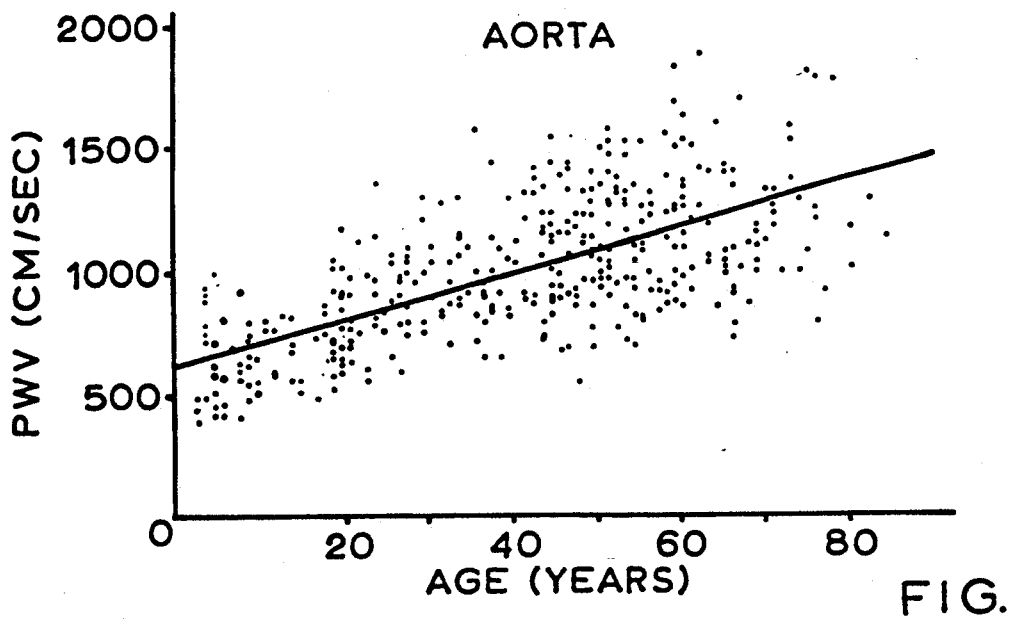
FIG. 2 is a graph of the distribution of aortic pulse wave velocity as a function of age.

FIG. 2 illustrates the change in the arterial pulse wave velocity with age. This change, which is attributable to a stiffening of the arteries with age, explains why the secondary wave peaks 5a and 5c (FIG. 1) occur for the youth and the older subject at different times during late systole. The secondary wave returns earlier in the older subject and it combines with, and thus augments, the systolic pressure peak.

Figures 3A, 3B:
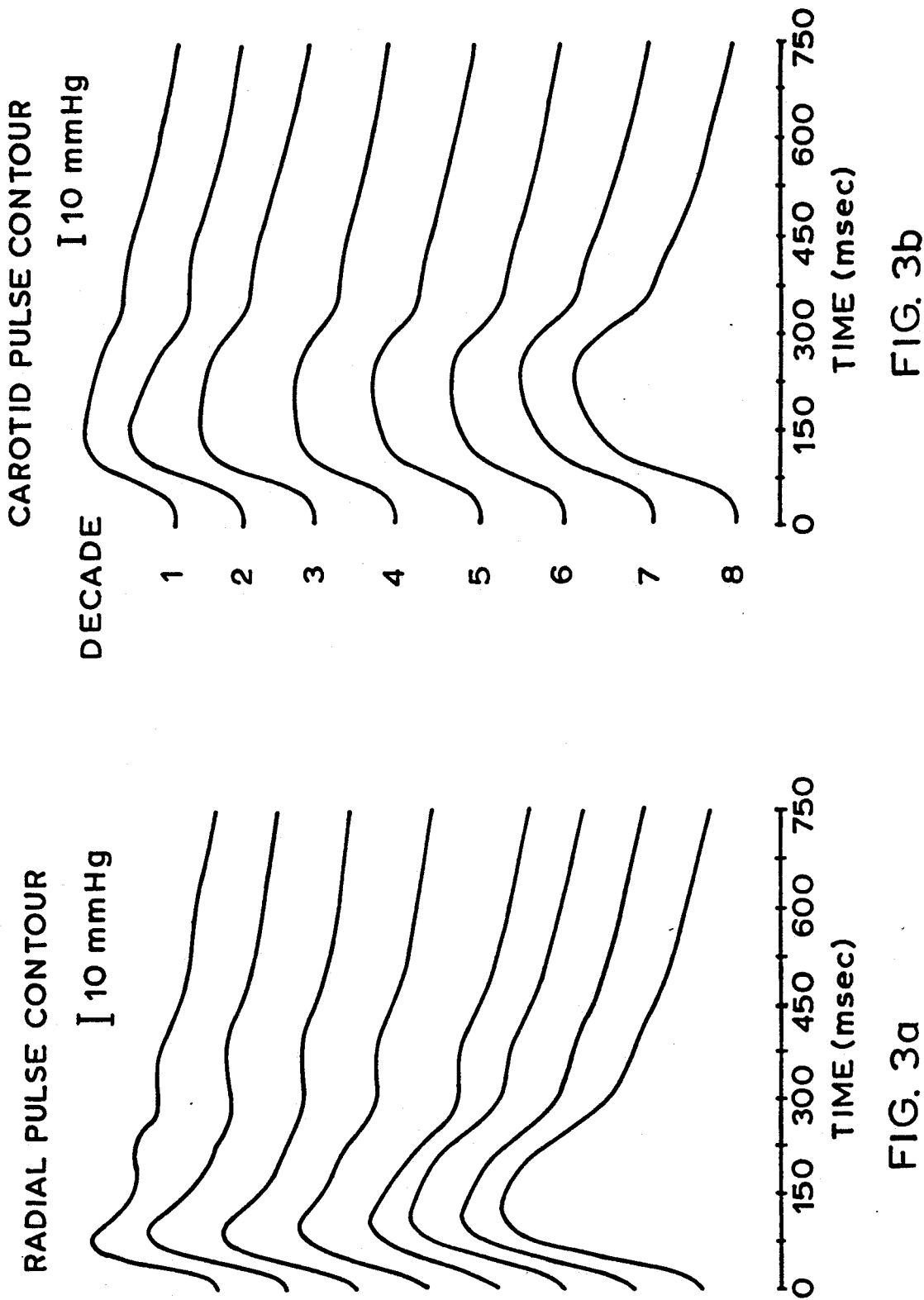
FIGS. 3a and 3b is a diagram of radial and carotid arterial pressure pulses at various ages.

FIG. 3 illustrates the characteristic changes in the contour of pressure pulses in the radial and carotid arteries over eight decades. The pressure pulses in the carotid artery are almost identical in shape to the pressure pulses in the ascending aorta. Late systolic augmentation is observed in the pressure pulses in the carotid artery from the fourth decade on. Such augmentation is not readily observed in the radial artery until the eighth decade.

Figure 4A:
FIGS. 4a and 4b are diagrams of the pressure waves in the ascending aorta and brachial artery before (left) and after (right) treatment with nitroglycerine.
Figure 4B:
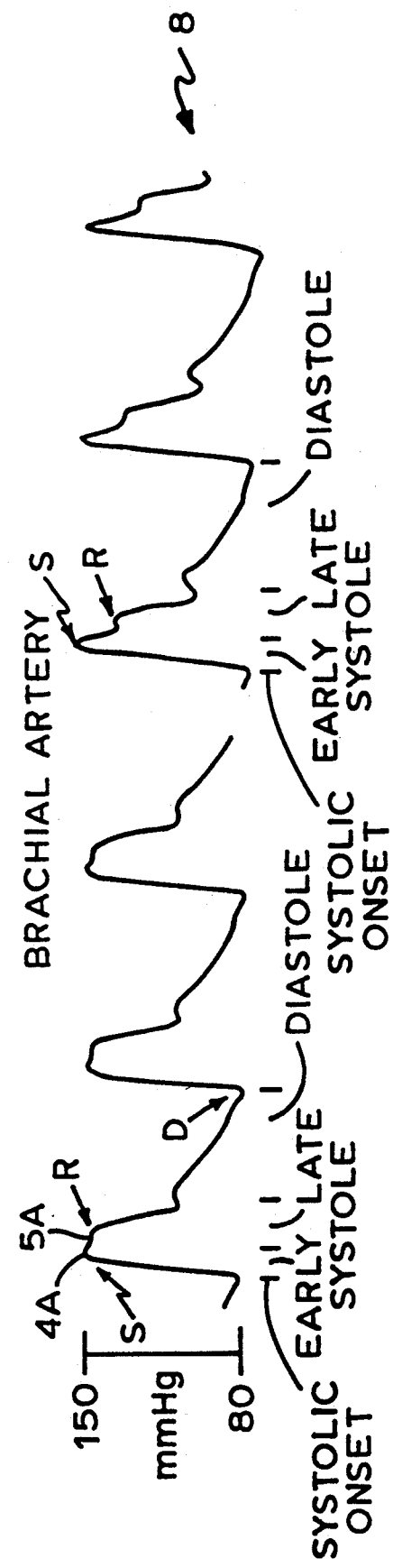

FIG. 4 illustrates an invasively measured ascending aorta pressure wave 7 and a corresponding pressure wave 8 in the brachial artery of an older subject, both before and after the subject ingests nitroglycerin (GTN). The pressure waves labeled "control" correspond to the pressures before the ingestion of the GTN and the waves labeled "GTN" correspond to the pressure after the ingestion of the GTN.

Referring now to the "control" waves, the brachial artery pressure wave 8 includes a series of pulses, each of which has a peak 4a in early systole and a secondary wave peak 5a in late systole which correspond to the peaks 4a and 5a of FIG. 1. The peak 5a in the brachial artery pulse indicates the return of the secondary wave from the lower part of the body. The points labeled S and D, that is, the maximum and minimum points, of the brachial artery pressure wave correspond with systolic and diastolic sphygmomanometer measurements of blood pressure.

When GTN is administered, it dilates the arteries, and thus it slows the primary pressure wave and also slows and markedly diminishes the reflected or secondary wave. Accordingly, the point labeled R on the brachial artery curves corresponding to the reflected wave is displaced downward and slightly to the right in the GTN curves. Due to the reduced amplitude of wave reflection and to its later return, the aorta does not experience as much pressure from this effect, and thus there is a noticeable reduction in the maximum pressure peak of the ascending aorta pressure wave.

While the reduction in amplitude and later arrival of the secondary wave results in a change in the shape or contour of the corresponding brachial artery pressure wave, the maximum pressure peak, labeled S, is not changed. Accordingly, the sphygmomanometer registers the same systolic pressure reading after the ingestion of GTN as before. Thus it does not register the effects of the GTN.

The effects of the GTN are noticeable in the reduction of the peak pressure in the ascending aorta, which can be directly measured using invasive systems. However, the effects are also noticeable in changes in the contour of the brachial artery and radial artery pressure waves, which can be measured either noninvasively using a tonometer or other similar device or invasively through an intra-arterial cannula. The present inventive system invention derives from measurements of the peripheral pressure wave the maximum and mean pressures in the ascending aorta. The system, also, synthesizes the contour of the pressure wave in the ascending aorta from the measured peripheral wave and determines directly from this synthesized wave the maximum ascending aortic pressure, and systolic and diastolic pressures and pressure-related indices. The system then calculates an augmentation index from pressure values relating to either the synthesized wave or the measured wave, or both.

2. Synthesizing the Contour of the Ascending Aortic Pressure Wave From the Contour of the Measured Peripheral Pressure Wave The contour of an ascending aortic pressure pulse can be synthesized from the measured peripheral pulse contour using either a frequency-domain calculation method or a time-domain calculation method. Referring now to FIG. 5, a transfer function processor 58 develops transfer functions relating peripheral pressure pulses and ascending aortic pressure pulses. The transfer function processor 58 accumulates both contours from a number of individuals. Specifically, invasively measured ascending aortic pressure pulses ("AA") and invasively and non-invasively measured carotid artery ("CA"), brachial artery ("BA") and radial artery ("RA") pressure pulses are accumulated.

Next, the processor 58 derives for each individual the Fourier transforms of the various aortic and peripheral pulse waves, and generates for each individual the transfer functions:

$$H^*(w)_{AA-BA} = BA(w)/AA(w)$$
$$H^*(w)_{AA-RA} = RA(w)/AA(w)$$
$$H^*(w)_{AA-CA} = CA(w)/AA(w)$$

where $AA(w)$, $BA(w)$, $RA(w)$ and $CA(w)$ are the Fourier transforms of the various pulses and $w$ is frequency. The transfer function processor 58 then, to account for differences in heart rates between individuals, applies a smoothing function to each group of corresponding transfer functions $H^*(w)_{AA-BA}$, $H^*(w)_{AA-RA}$ and $H^*(w)_{AA-CA}$, and generates a set of generalized transfer functions, $H(w)$. Thereafter the system uses these transfer functions, $H(w)$, to synthesize ascending aortic pressure pulses from measured peripheral artery pressure pulses.

Figure 6A:
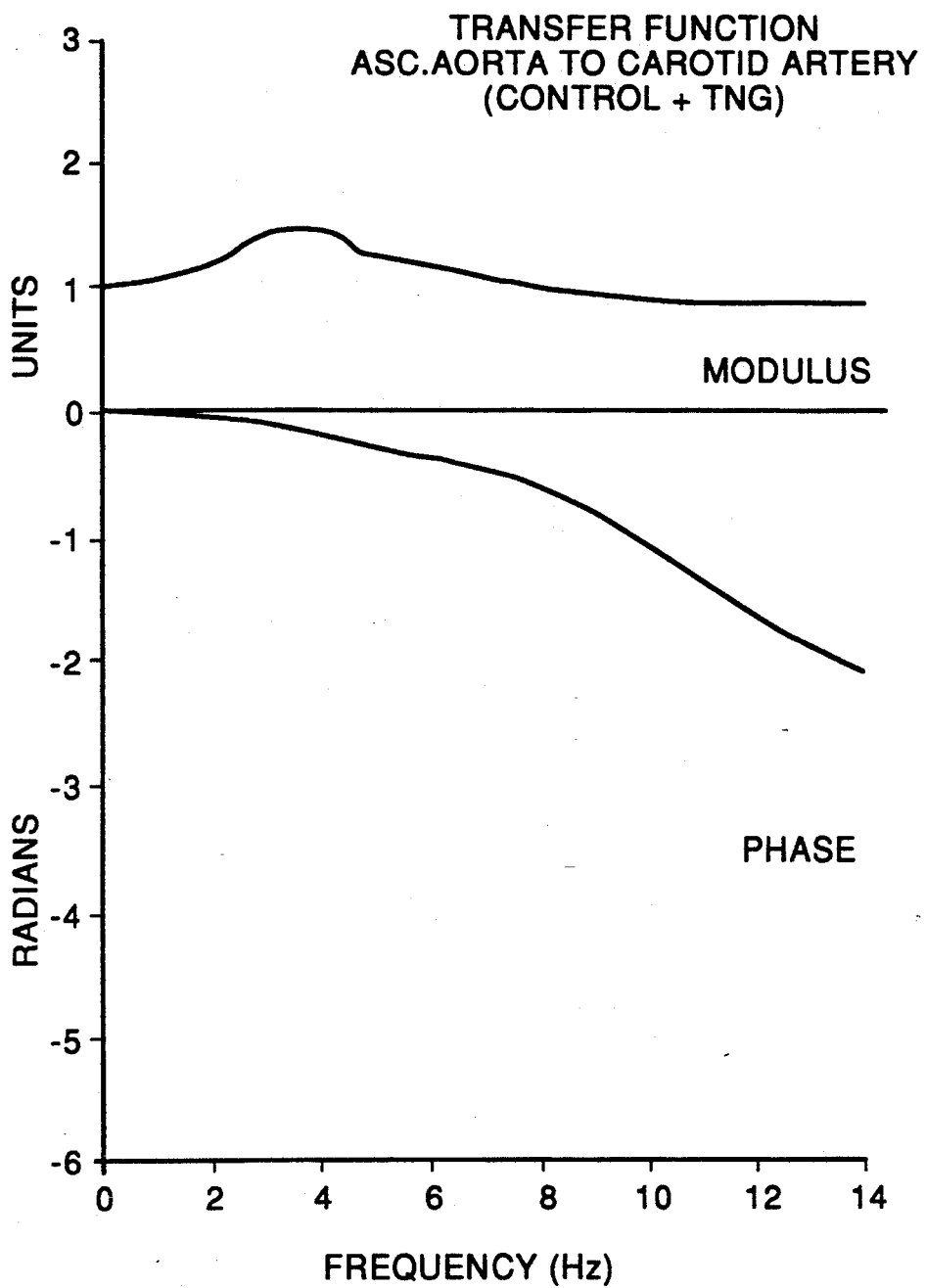
FIGS. 6A-C depict graphically transfer functions for ascending aorta to peripheral artery pressure pulses.
Figure 6B:
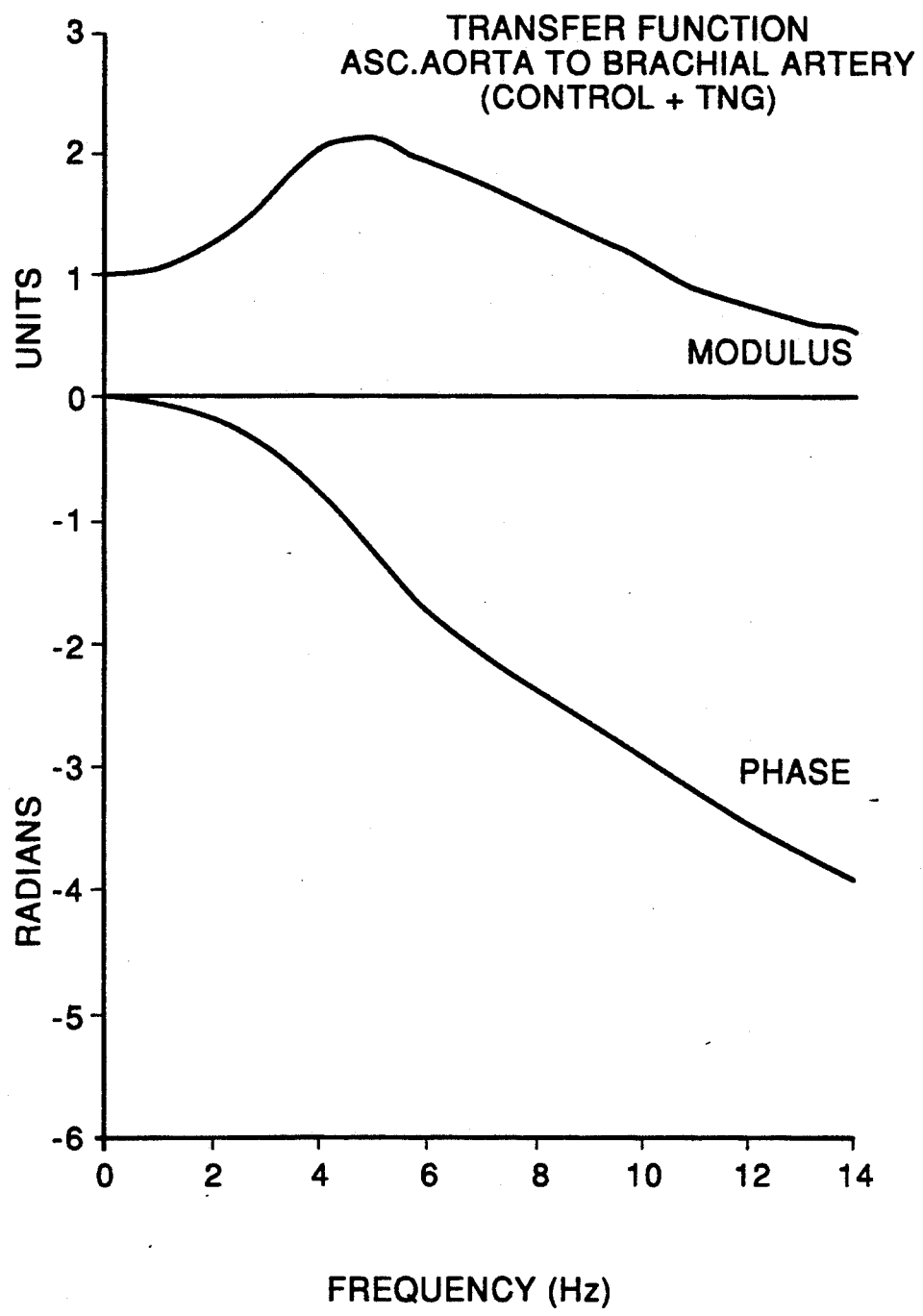
Figure 6C:
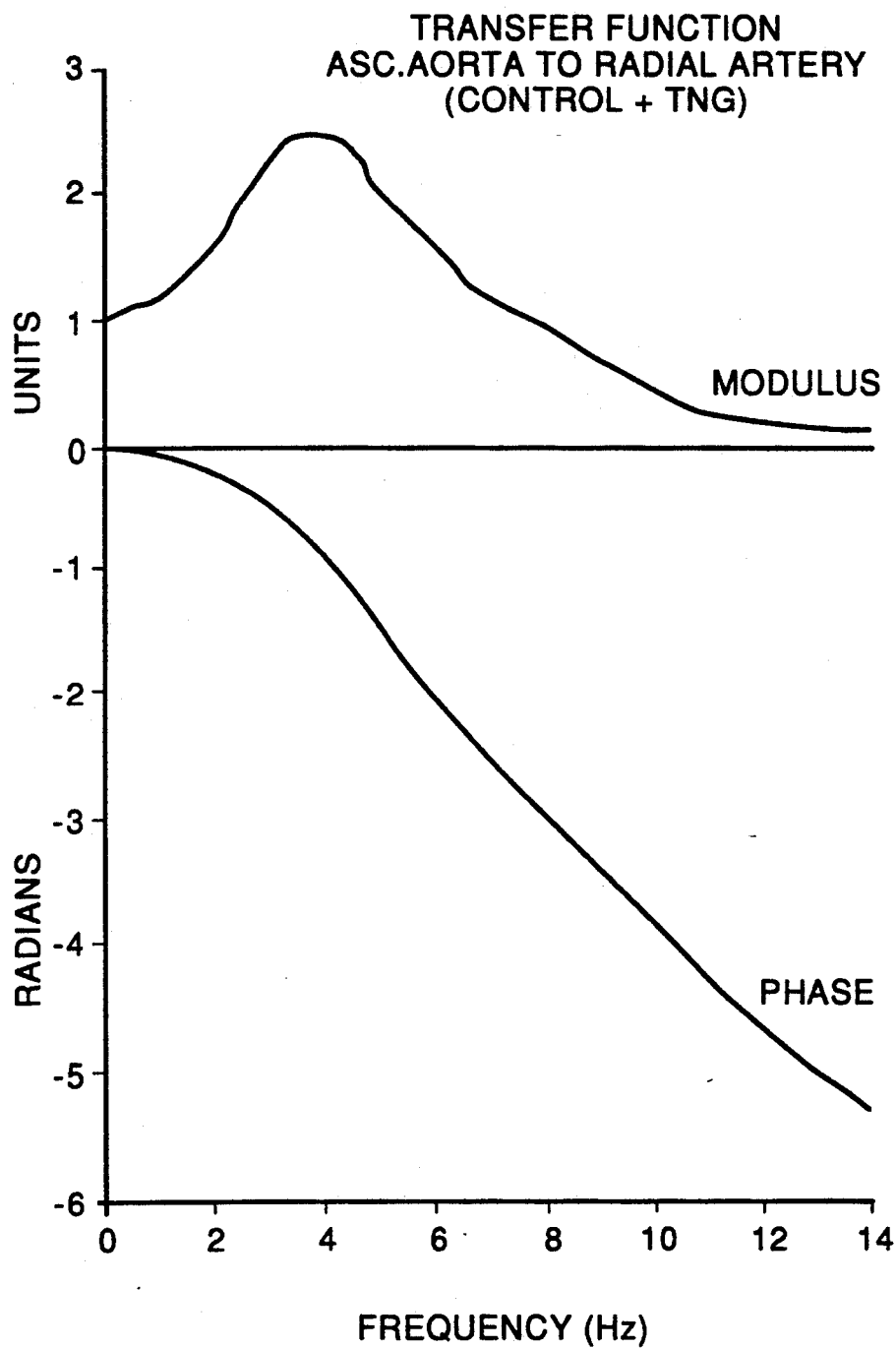

FIGS. 6A–C are graphs of a set of generalized transfer functions, $H(w)$. Specifically, FIG. 6A is a graph of $H(w)_{AA-CA}$, FIG. 6B is a graph of $H(w)_{AA-BA}$ and FIG. 6C is a graph of $H(w)_{AA-RA}$. Measurements were taken and separate transfer functions derived for two groups of patients, namely, a group of patients being treated with nitroglycerin (the GTN/TNG group) and a group of patients not being treated with nitroglycerin (the control group). The two sets of transfer functions were virtually identical to each other. From these results one can conclude that the depicted transfer functions are generally applicable. Use of generalized transfer functions at different ages is supported by the finding that upper limb pulse wave velocity changes little with age in contrast to aortic wave velocity (FIG. 2).

Referring now to FIG. 7, the pressure pulse in the ascending aorta may be synthesized from measured peripheral artery pulses using either a frequency-domain calculation method or a time-domain calculation method. Using the frequency-domain calculation method, peripheral pulse wave information, from either an invasive or a non-invasive measuring device, is applied to a Fourier transform processor 60. The processor 60 then derives the Fourier transform of the peripheral wave, for example, $BA(w)$.

The Fourier Transform, BA(w), and the corresponding transfer function, $H(w)_{AA-BA}$, are applied to an Inverse Fourier transform processor 62, which first divides the derived Fourier transform, BA(w), by the transfer function, producing the Fourier transform of the corresponding ascending aortic pressure pulse, AA(w). The processor 62 then calculates the inverse Fourier transform of AA(w), to obtain the time domain representation of the aortic pressure pulse, AA(t). The time domain information may be displayed graphically as shown by curve 64 in FIG. 8, which is a synthesized ascending aorta pulse corresponding to the brachial artery shown, in graphic form, in FIG. 9.

Figure 8:
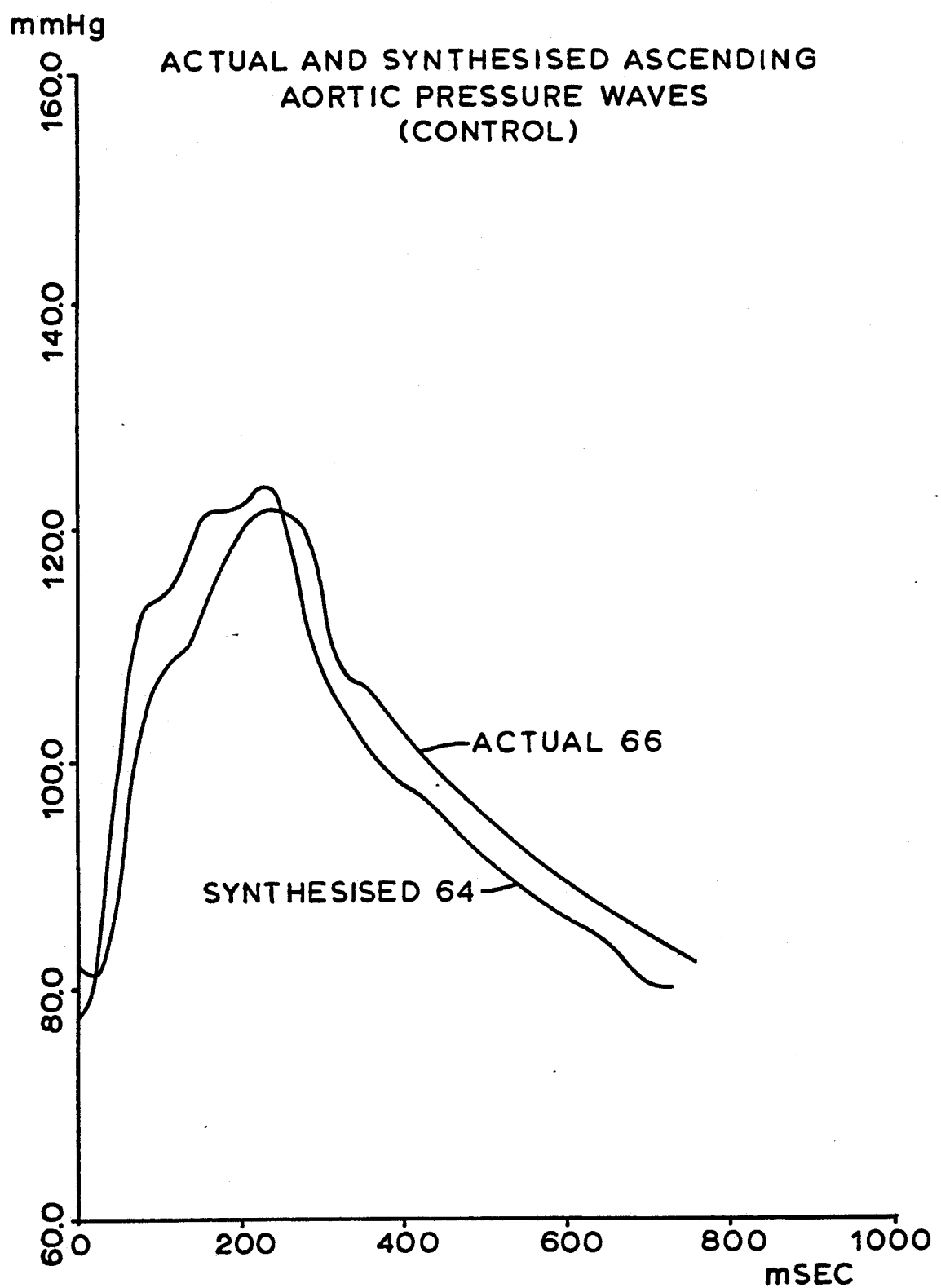
FIGS. 8-15 depict graphically measured and synthesized aortic pressure pulses and corresponding measured peripheral pulses.
Figure 9:
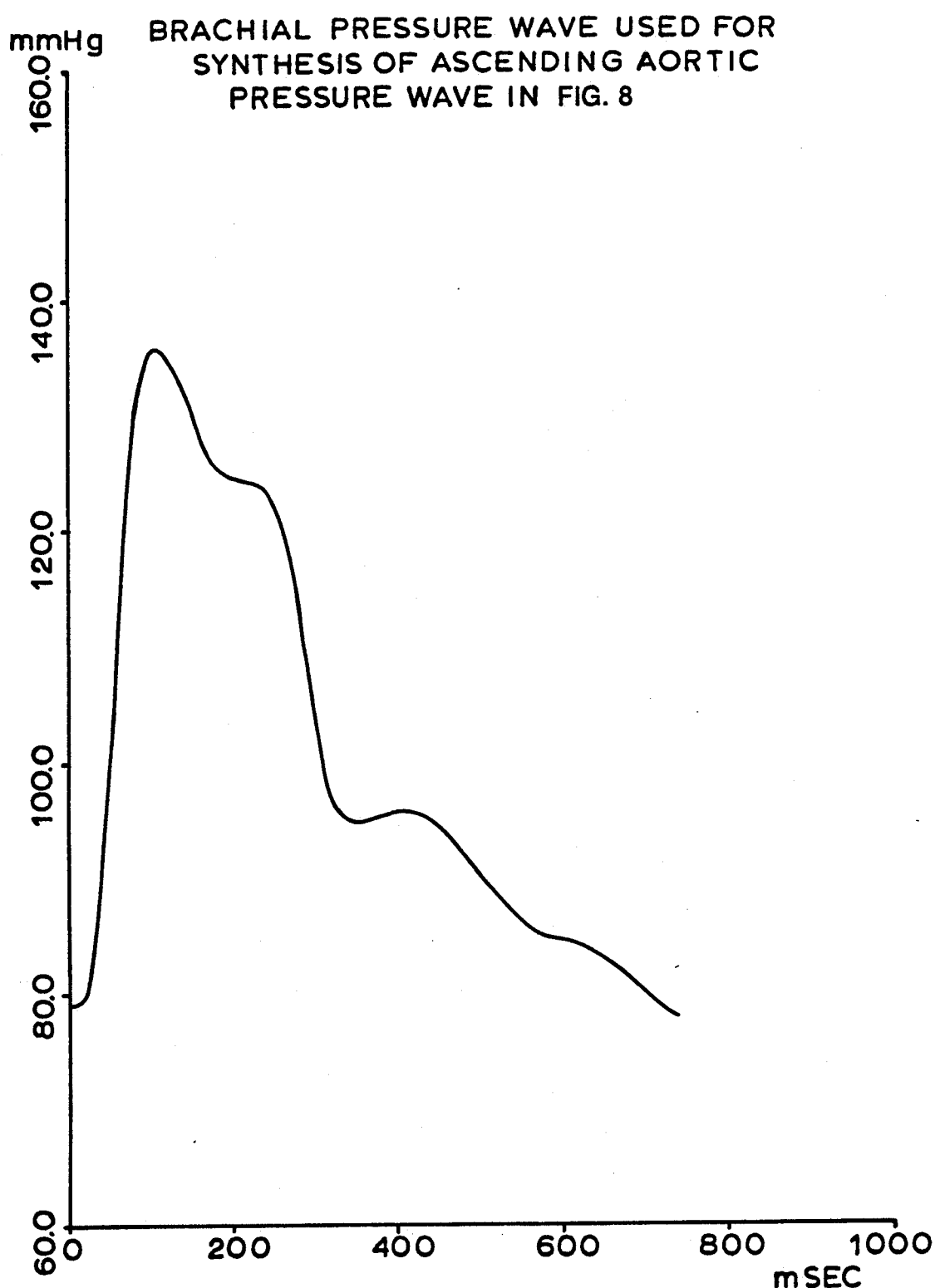
Figure 10:
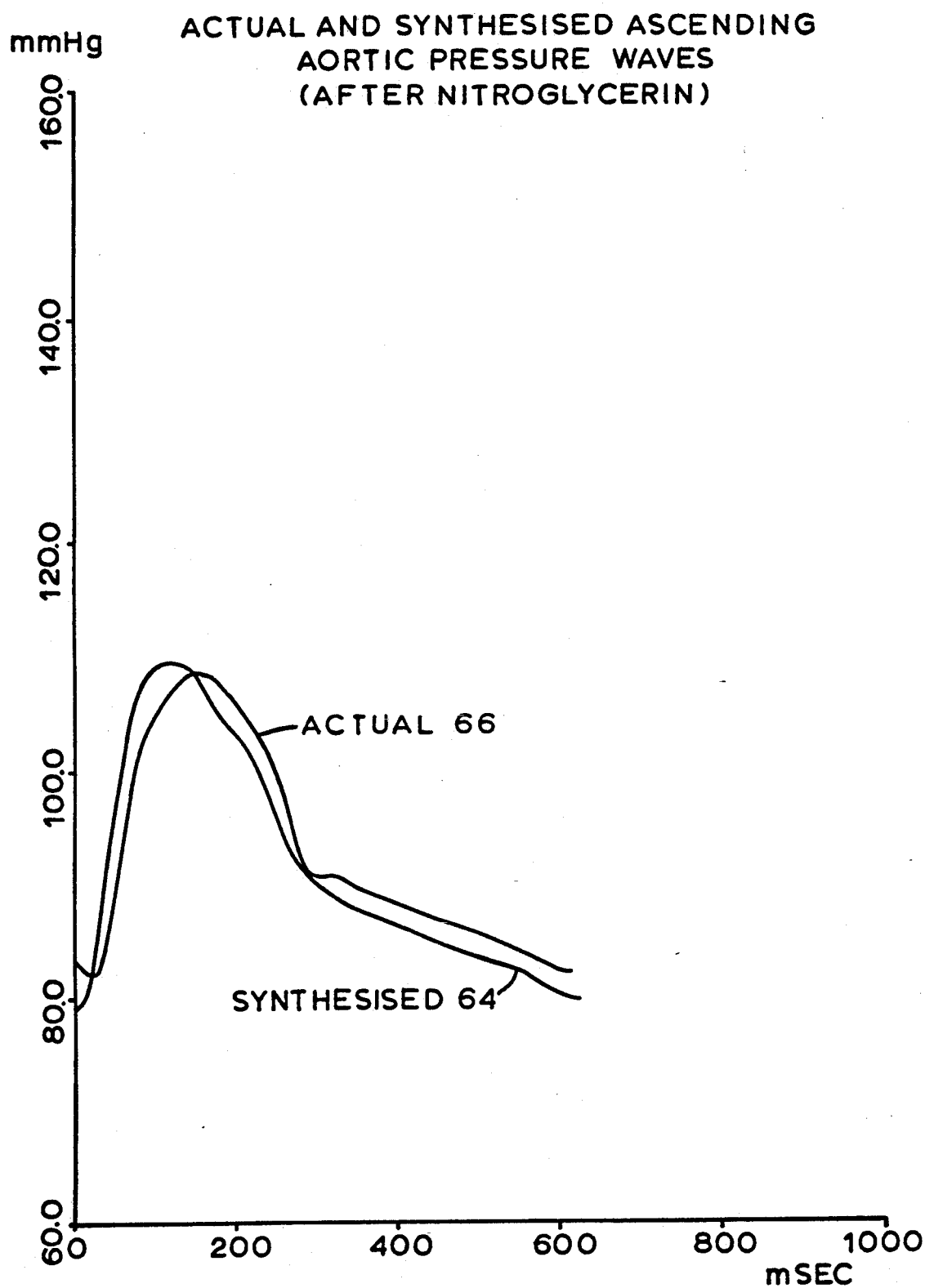
Figure 11:
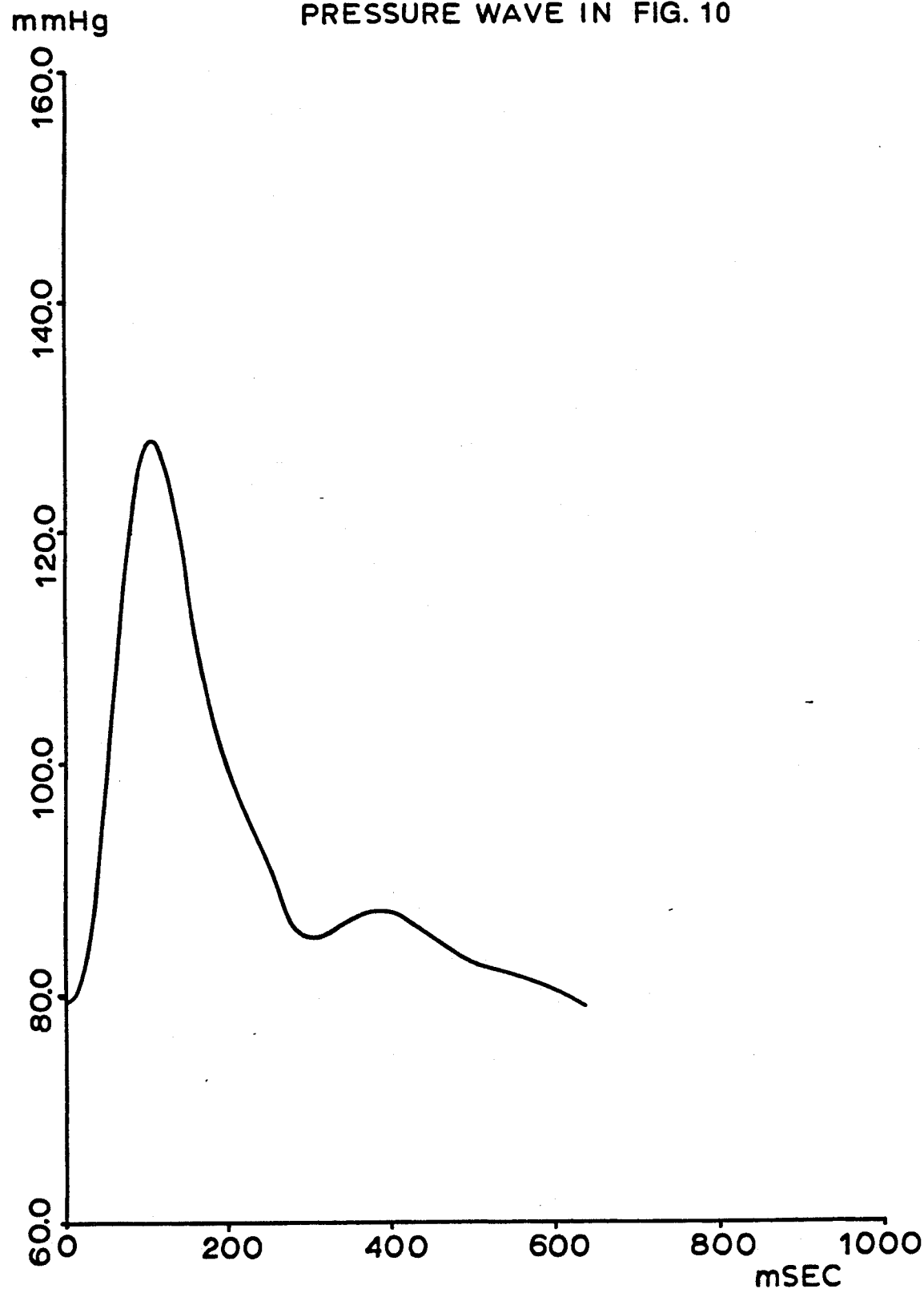
Figure 12:
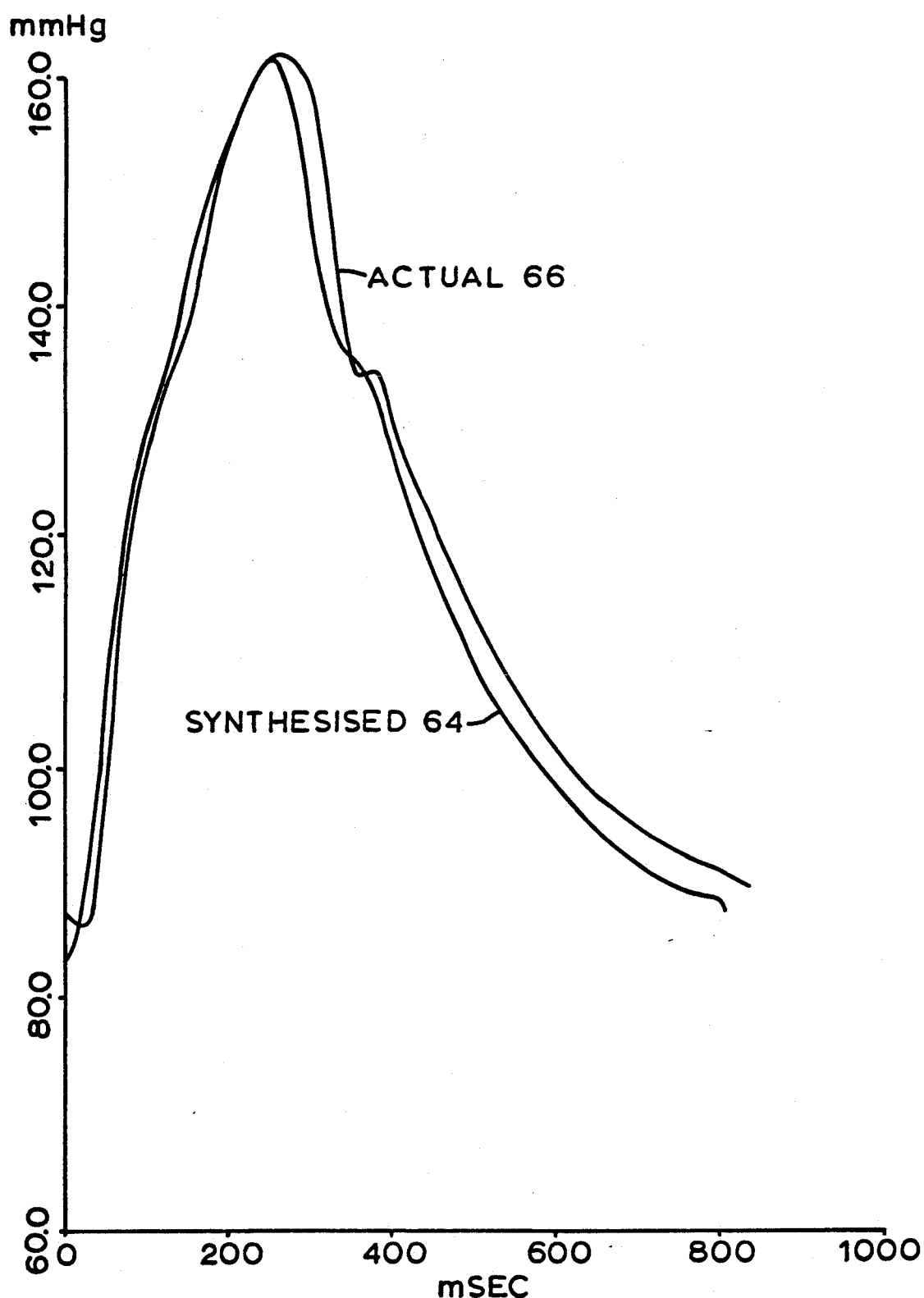
Figure 13:
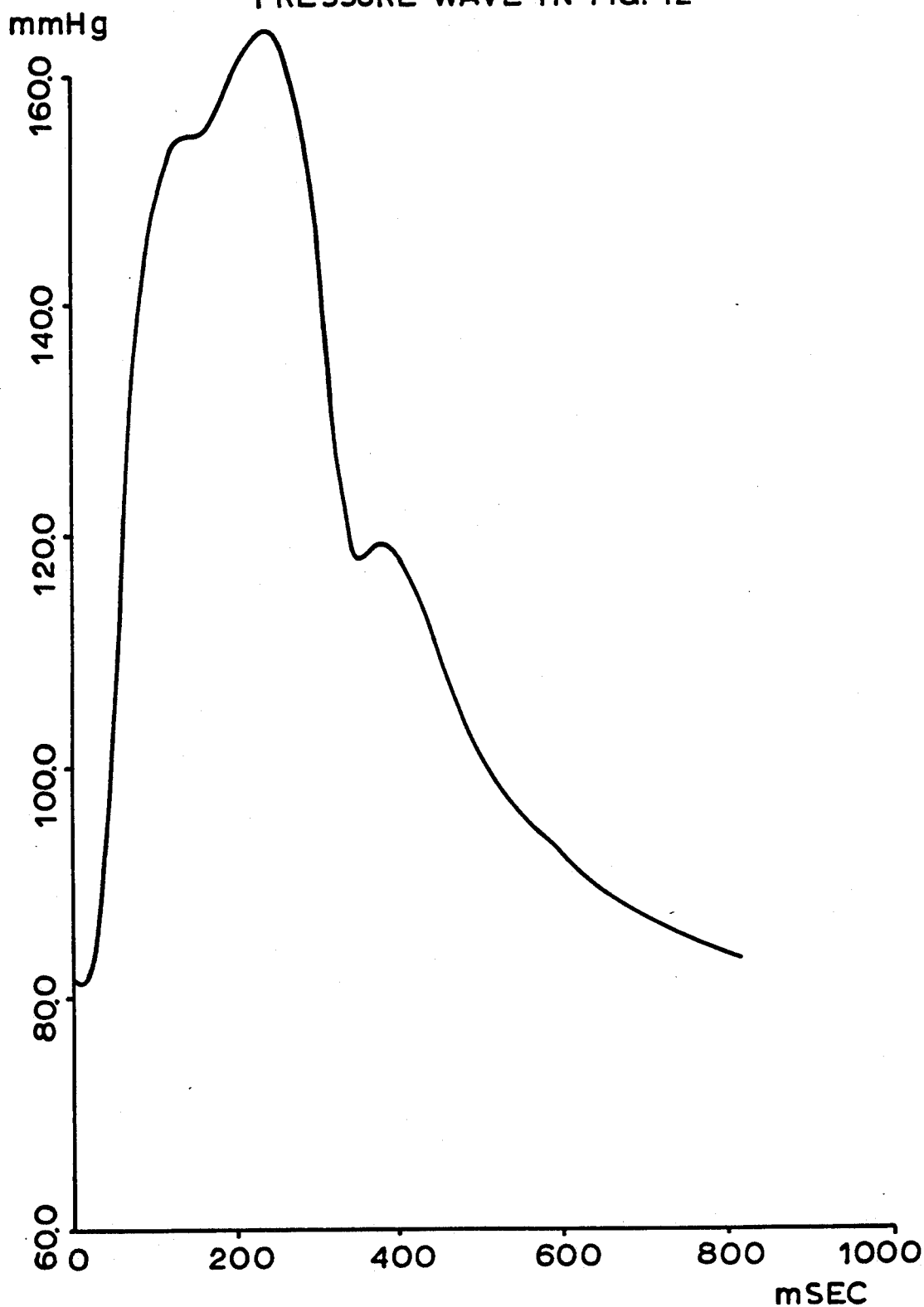
Figure 14:
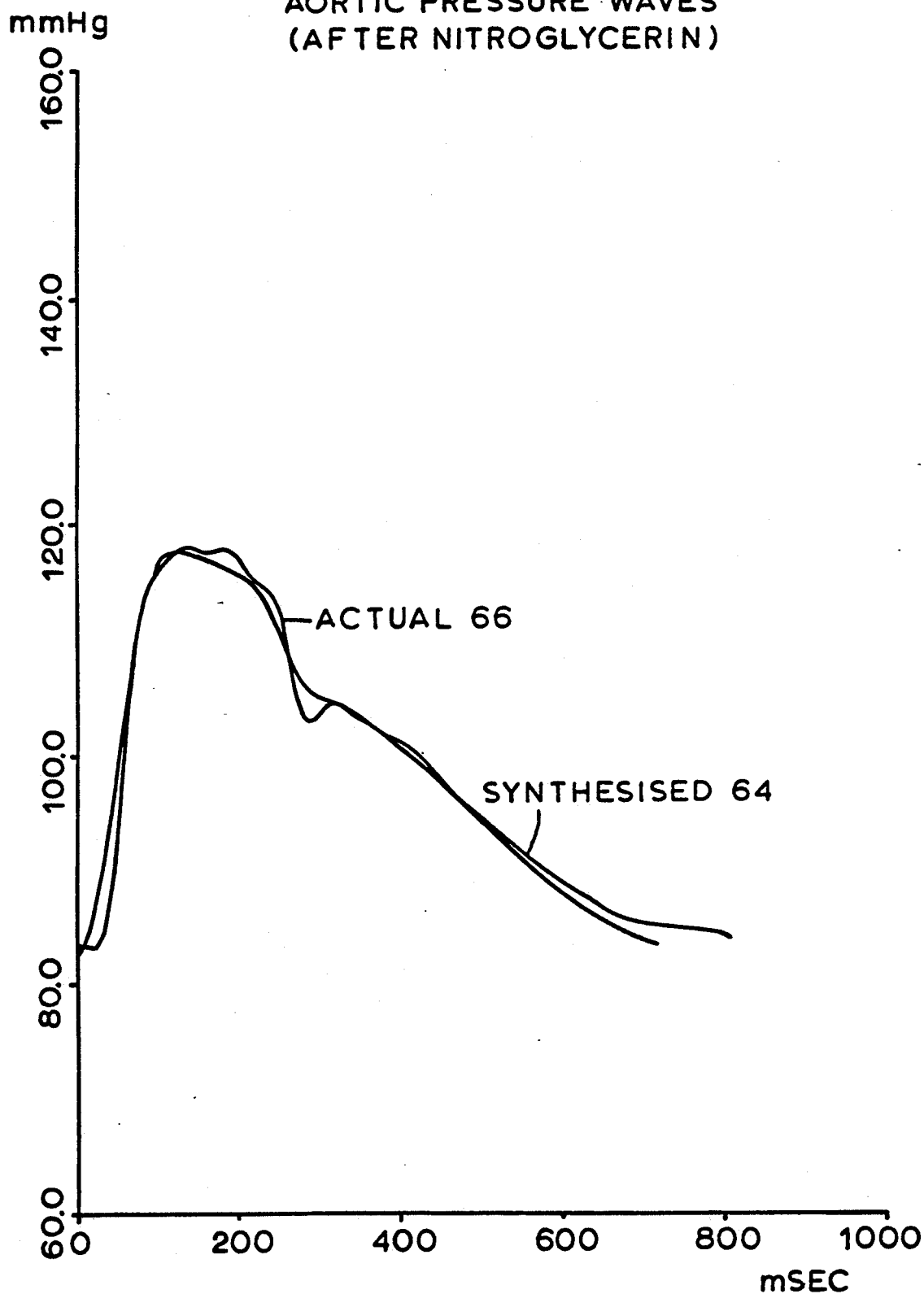
Figure 15:
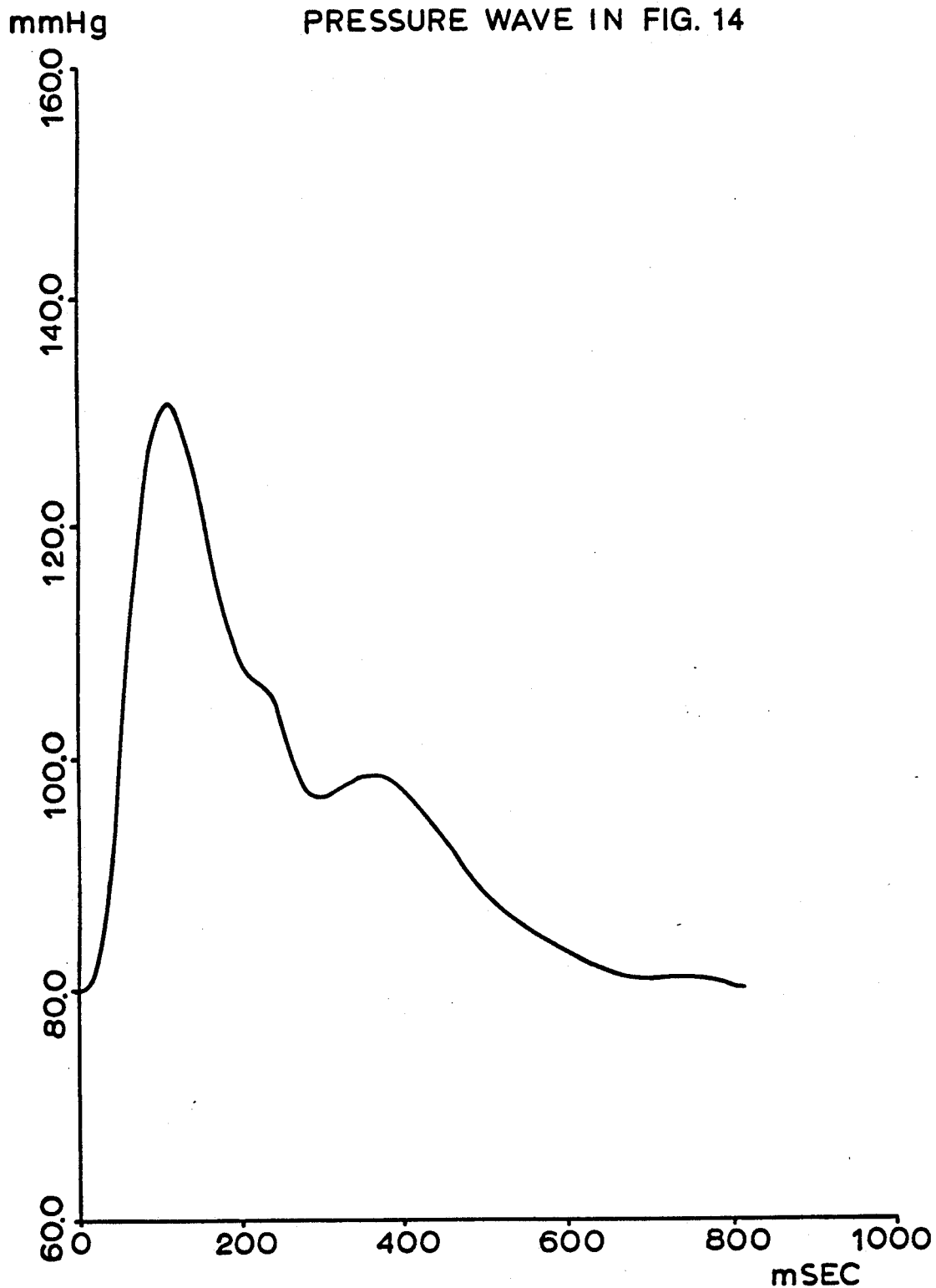

Referring again to the exemplary curve 64 of FIG. 8, using this frequency-domain calculation method the system produces, with a lag time of approximately one heart beat, the synthesized ascending aortic pressure pulse 64 which closely resembles the actual (invasively measured) ascending aortic pressure pulse, a graph of which is shown as curve 66 in FIG. 8.

Alternatively, the ascending aortic pressure pulse may be synthesized by convolving the inverse Fourier transform of the multiplicative inverse of the appropriate transfer function, for example, $H(w)_{AA-BA}$, with the time domain representation of the measured peripheral artery pressure pulse, BA(t), as shown in FIG. 7. Using the time domain method of synthesizing the ascending aortic pressure pulse, the system produces the synthesized ascending aortic pressure pulse in essentially real time, that is, without a lag time of a full heart beat.

FIGS. 8-15 are graphs of synthesized aortic pressure pulse waves (curves 64) and corresponding actual aortic pressure pulse waves (curves 66) and the corresponding brachial artery pressure pulses. As can be seen, the synthesized waves closely resemble the actual aortic pressure waves in all cases.

Observing graphs of both the contour of the measured peripheral wave and the synthesized contour of the aortic pressure wave, it is difficult in many instances to locate the two pressure peaks in systole and the incisura, which indicates the onset of diastole. Further, it is difficult to determine by observation if the aortic pressure is augmented and the degree of the augmentation. Accordingly, the system determines the locations of the incisura and the systolic peaks, and, calculates various pressure and augmentation indices based on manipulations of either or both of the measured peripheral pressure pulses and the synthesized aortic pressure pulses.

Figure 16:
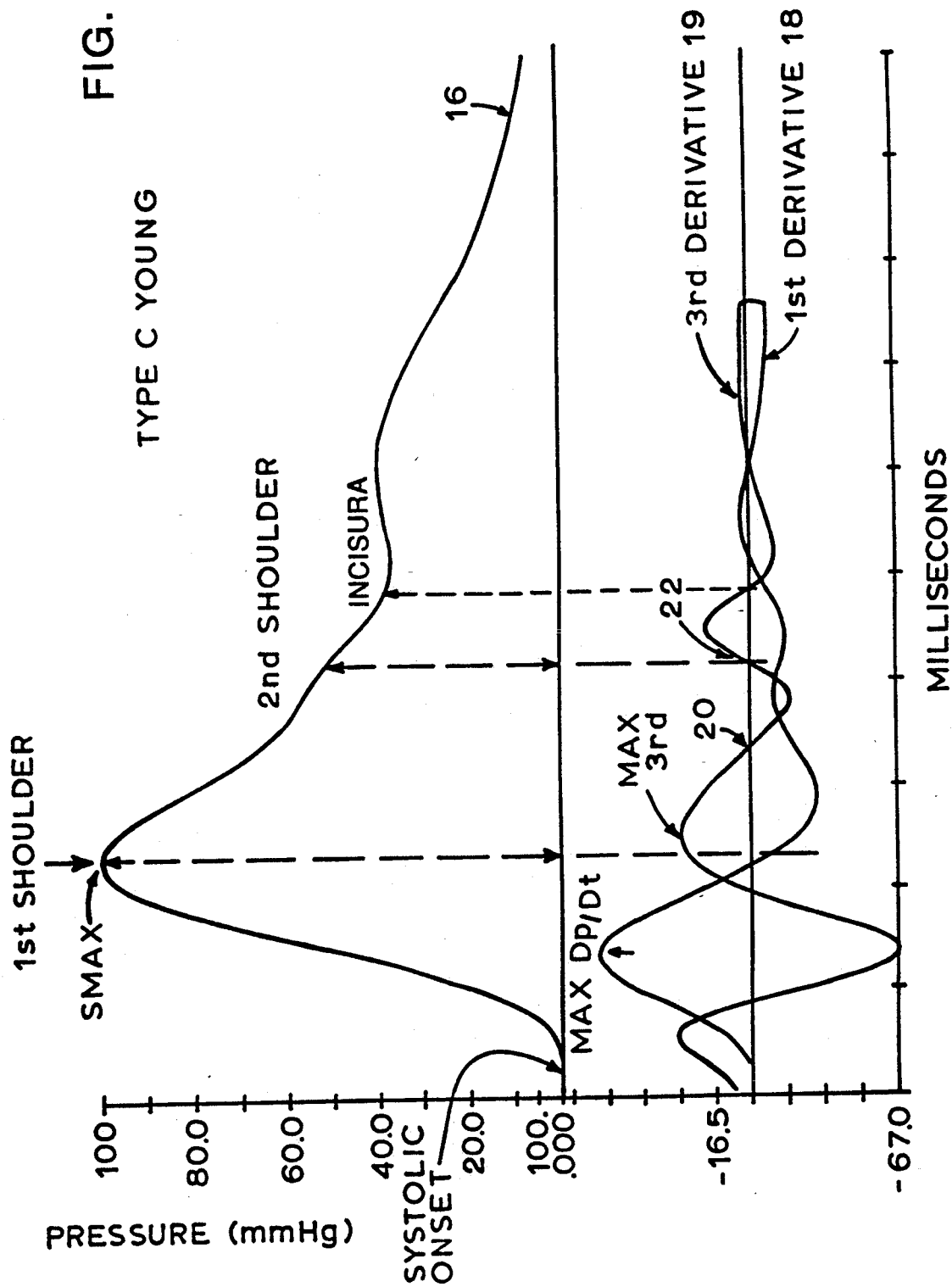
FIG. 16 is an illustration of an average brachial artery pressure pulse of a youth and the first and third derivatives of the pulse.
Figure 17:
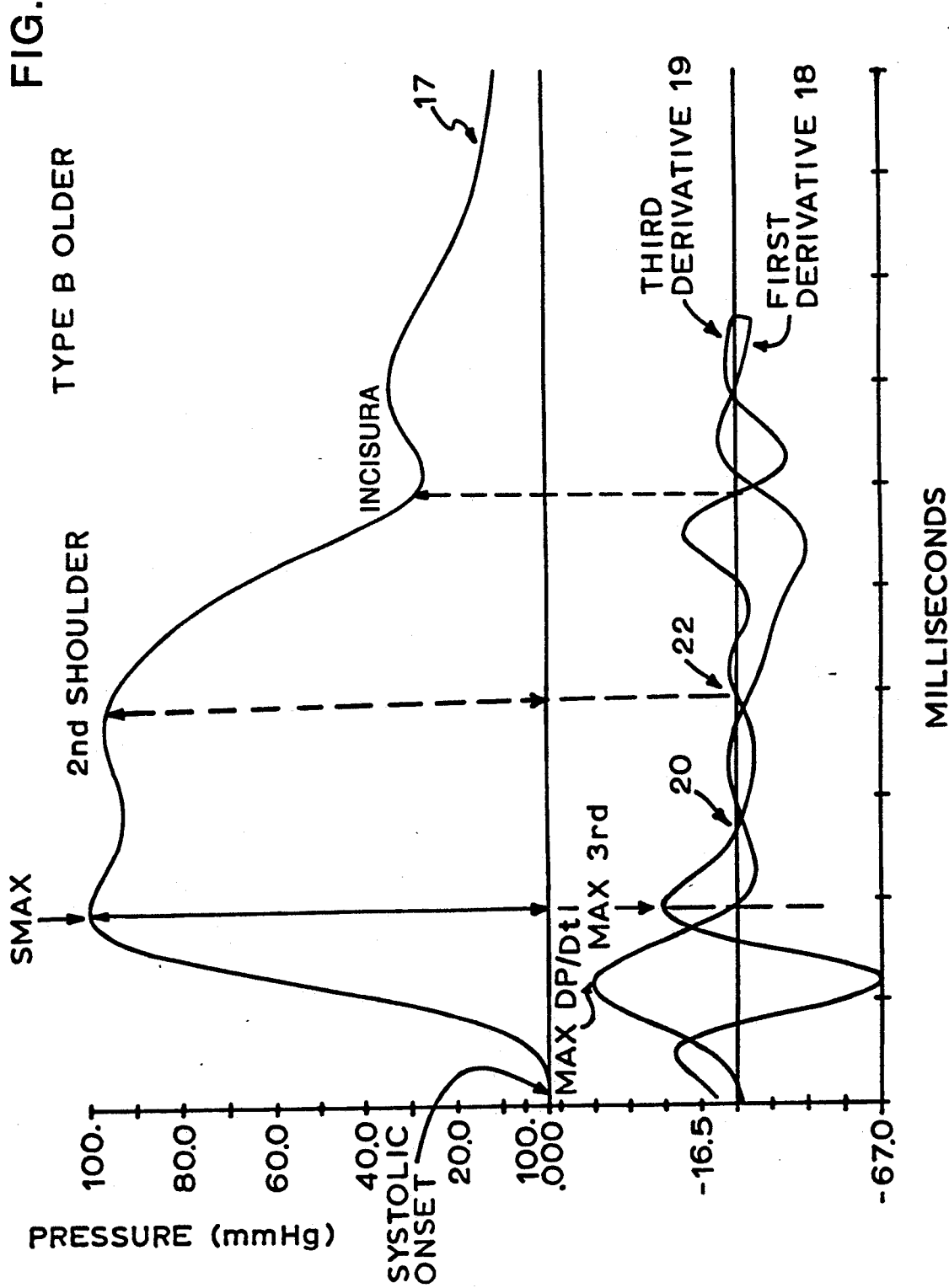
FIG. 17 is an illustration of an average brachial artery pressure pulse of an older subject and the first and third derivatives of the pulse.
Figure 18:
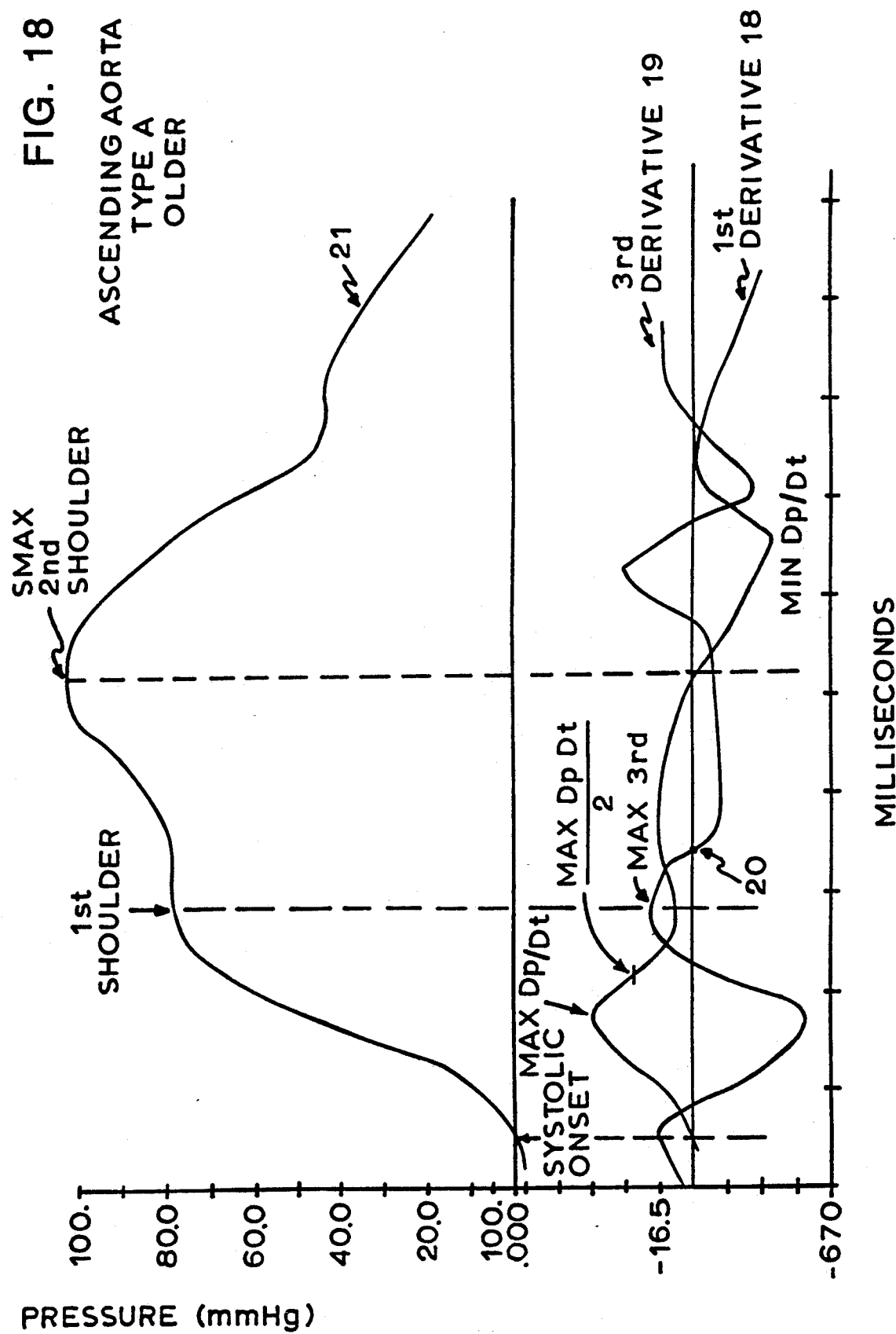
FIG. 18 is an illustration of the ascending aortic pressure pulse corresponding to the brachial artery pressure pulse shown in FIG. 17 and the first and third derivatives of the pulse.
Figure 19:
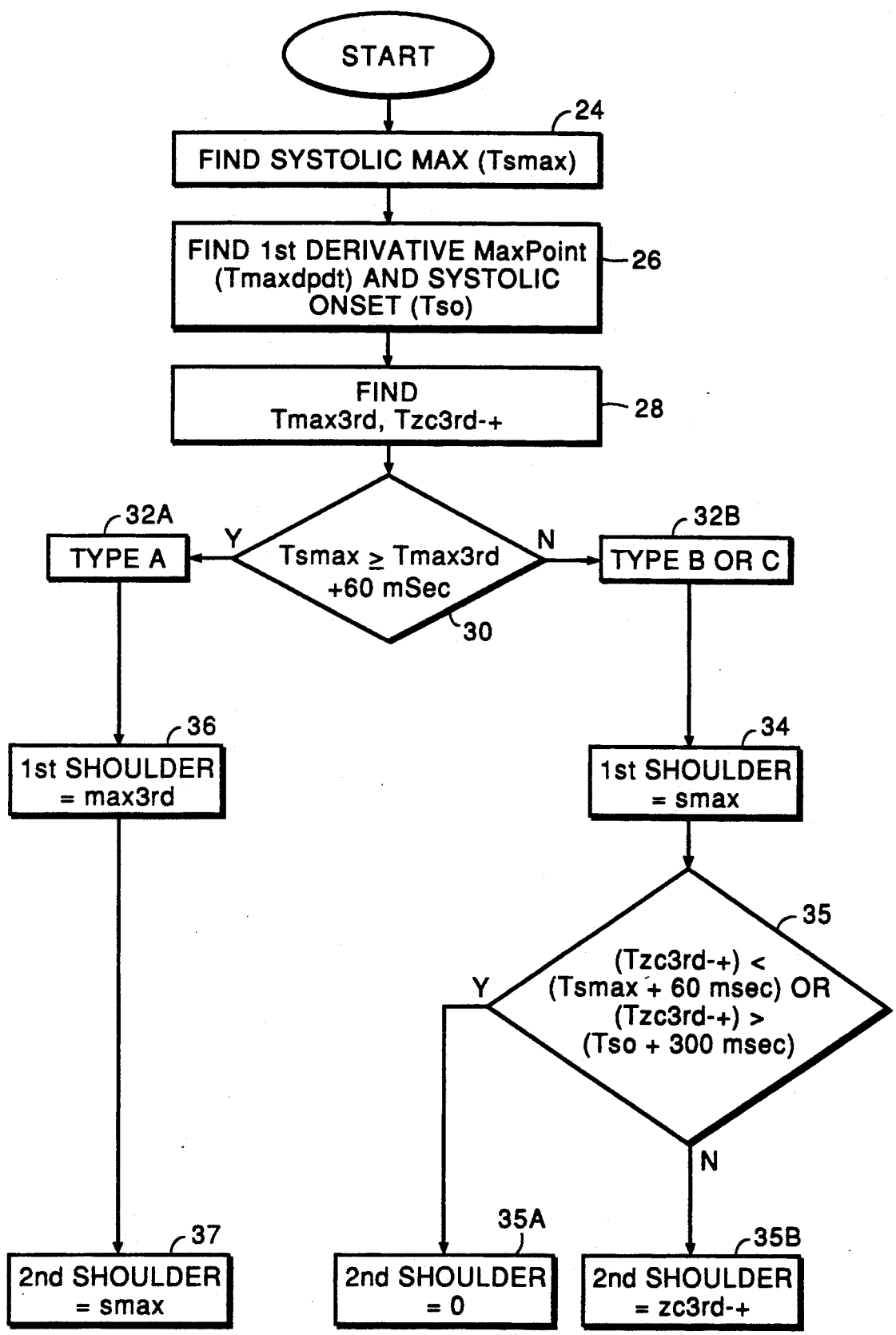
FIG. 19 is a flow chart for determining the locations of first and second shoulders in the average pressure pulses shown in FIGS. 16 and 17.
Figure 20:
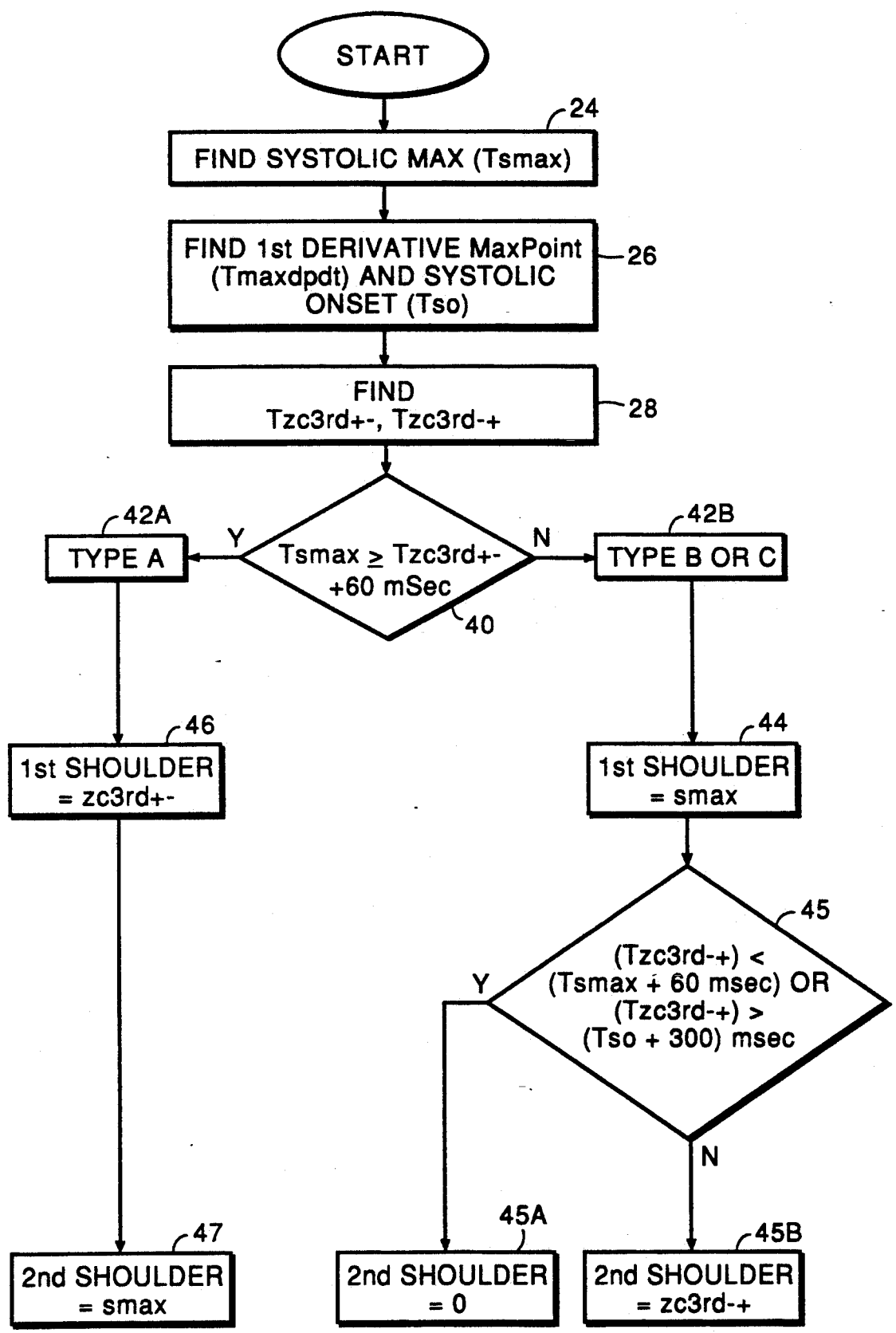
FIG. 20 is a flow chart depicting an alternative mechanism for determining the locations of the first and second shoulders.

3. Formulating Ascending Aortic Pressure From Peripheral Pressure Wave Measurements And Measurements of the Synthesized Aortic Pressure Wave FIGS. 16-20 depict the steps which the inventive system performs in ascertaining pressure wave augmentation in the ascending aorta and various systolic and diastolic pressure-related indices. FIGS. 16 and 17 illustrate graphically the method of determining from the peripheral pulses locations of the pressure peaks and the degree of augmentation; FIG. 18 illustrates graphically the method of determining from the synthesized aortic pressure pulses the locations of the pressure peaks and the degree of augmentation; and FIGS. 19 and 20 are flow charts of the steps performed by conventional processors (not shown) in ascertaining pressure wave augmentation.

FIGS. 16 and 17 illustrate peripheral artery pressure pulses 16 and 17, respectively, and FIG. 18 illustrates synthesized ascending aorta pressure pulse 20. These pulses are "average" pulses, determined by ensemble averaging the pulses from the related measured or synthesized pressure waves. Each average pulse has two peaks in systole, a primary pressure peak, labeled "first shoulder," and a secondary pressure wave peak, labeled "second shoulder." The relative amplitudes of the two peaks are analyzed to ascertain the amount of ascending aortic pressure augmentation.

Before the two systolic peak amplitudes can be analyzed, however, they must be located. First, the system locates on the peripheral pulse the start of the pulse or "wave foot", which indicates the onset of systole. The system also determines using either the peripheral pulse or the synthesized pulse the relative maximum points of the pulse in systole. Next, the system locates on the peripheral pulse the incisura, which indicates the end of systole and the beginning of diastole. Using these points, the system determines the time between the wave foot and the incisura, and then segments the synthesized pulse into a systole component, which corresponds to the time between the foot and the incisura, and a diastole component, which corresponds to the cycle time after the incisura.

The various pulse points can be found by analyzing the first and third derivatives of the pulses. In the Figures, the first derivative is labeled curve 18 and the third derivative is labeled curve 19. The pulse relative maximum (and minimum) points correspond to the zero crossings of the first derivative curve 18. The maximum point of the first derivative curve corresponds to the point of maximum pulse slope, that is, the point in early systole at which the pulse is rising most steeply to its first peak. The point of systolic onset, which is also referred to as the wave foot, corresponds to the first negative-to-positive zero crossing which precedes the first derivative maximum point. The first derivative maximum point is labeled "MAXdp/dt" in FIGS. 16-18.

Once the point of systolic onset is located, the absolute maximum pulse point is determined. This is the point which corresponds to the point labeled S in FIG. 4, that is, the maximum systolic pressure, which is labeled SMAX in FIGS. 16-18. The maximum point, SMAX, may or may not correspond to the first peak of the pressure pulse. In order to positively identify the first pulse peak, the system examines the third derivative curve 19. The third derivative curve 19 has a relative maximum at or near the location which corresponds to the first pulse peak. This relative maximum point is labeled "MAX3rd" in FIGS. 16-18.

If the MAX3rd point is close, in time, to the SMAX pulse point, then the pulse has the shape shown in FIGS. 16 and 17 (type B or C). If the MAX3rd point is not close, in time, to the SMAX point the pulse has the shape shown in FIG. 18 (type A). Referring again to FIGS. 16 and 17, if the first peak corresponds to the SMAX point the point is labeled as the first shoulder, and the second shoulder is located by finding the pulse point corresponding to the first negative-to-positive zero crossing 22 of the third derivative 19 thereafter.

If the first shoulder does not correspond to SMAX, as in the pulse shown in FIG. 18, the second shoulder corresponds to SMAX. Thus the first shoulder is located at or near the pulse point corresponding to the MAX3rd point and the second shoulder is located at the SMAX point.

After identifying the first and second shoulders, the system locates the incisura, which corresponds to the point at which the left ventricle ends its contraction and begins to relax. The incisura is indicated by a high frequency "notch" in the aortic pressure pulse, which is most easily detected in the measured radial, brachial or carotid artery pressure pulse. The system determines the location of the incisura by locating in the third derivation of the radial, brachial or carotid artery pressure pulse the positive-to-negative zero crossing following with the largest maximum after the second shoulder. If the second shoulder can not be identified, the system selects as the incisura the positive-to-negative zero crossing following the largest maximum point of the third derivative after the first shoulder.

The incisura occurs at approximately the one-third point in the heart pumping cycle, i.e., if the pumping cycle takes from systolic onset to the end of diastole time "$T_{cycle}$" the incisura should occur at approximately $\frac{1}{3} T_{cycle}$. Thus the system rejects as indicators of the incisura zero crossing points which are not within a predetermined time of the expected time of occurrence. In the preferred embodiment, the system rejects as incisura zero crossing points which are not within $+0.2(\frac{1}{3}T_{cycle})$ of the expected time of occurrence.

Once the first and second shoulders are determined, the amount of augmentation can be ascertained by comparing (i) the amplitude of the second shoulder, measured above the amplitude of the pulse at systolic onset, with (ii) the amplitude of the first shoulder, measured above the amplitude of the pulse at systolic onset. If the ascending aortic pressure is augmented this ratio is greater than "100%." The computation of the amount of augmentation is explained in more detail below with reference to FIG. 21.

FIG. 19 is a flow chart for determining the locations of the first and second shoulders of the arterial pressure pulse. The various calculations are performed by one or more processors, which are of conventional design. First, a tonometer or an intra-arterial cannula or other device (not shown) measures the contour of the pressure wave in a peripheral artery, for example, in the radial artery. The tonometer or cannula or other device produces an analog wave form which it applies to a processor which digitizes, filters, and ensemble averages it by pulses to form an average pulse signal. If a tonometer is used and its calibration is unknown, the processor normalizes the average pulse to the systolic and diastolic pressure readings of a sphygmomanometer.

The system also generates a calibrated synthesized aortic pressure wave and from this produces an average aortic pulse, following the same processes. The system can perform the same pulse analysis using values ascertained from this synthesized pulse as it performs using the measurement pulse, as described in more detail below.

The processor may use one of two alternative processes to determine the type of pulse and the locations of shoulders, as depicted in the flow charts of FIGS. 19 and 20. These alternatives include the expected times of occurrence of the primary pressure peak (first shoulder) after systolic onset and the reflected pressure peak (second shoulder) after the primary peak. The processor, using either the average peripheral pulse or synthesized pulse, finds the pulse maximum, SMAX and its time of occurrence, $T_{smax}$ (step 24). The processor then takes the first derivative of the average pulse and locates the maximum point, MAXdp/dt, and determines its time of occurrence, $T_{maxdpdt}$. Next, the processor locates the point of systolic onset by finding the first negative-to-positive zero crossing of the first derivative curve 18 immediately before MAXdp/dt, and determines the time of occurrence of systolic onset, $T_{so}$.

Using a first alternative process, as set forth in FIG. 19, the processor takes the third derivative of the pulse (curve 19 in FIGS. 16-18), locates the MAX3rd point, and determines its time of occurrence, $T_{MAX3rd}$, which is the time of the first relative maximum point of the third derivative Which succeeds the MAXdp/dt point (step 28). The processor also locates the point of zero crossing of the third derivative from negative-to-positive immediately following the MAX3rd point, Zc3rd-+ (point 22 in FIGS. 16-18), (step 28). Next the processor determines if SMAX precedes MAX3rd by 60 milliseconds or more, that is, if $T_{SMAX}+60$ msec $\leq T_{MAX3rd}+60$ msec (Step 30). If SMAX follows MAX3rd by 60 milliseconds or more, the processor determines that the pulse is a Type A, as shown in FIGS. 1 and 18 (steps 30-32A). Otherwise, the processor determines that the pulse has a shape which is associated with an younger subject, that is, the shape of the Type B or C pulse shown in FIGS. 1 and 16-17 (steps 30-32B).

If the pulse is Type B or C, the processor equates the first shoulder point, which is the point associated with the peak of the primary pressure wave, with the SMAX point (step 34). The processor then compares the time of occurrence of Zc3rd-+, that is, $T_{zc3rd-+}$, with $T_{smax}$ and $T_{so}$. If $T_{zc3rd-+}$ follows $T_{smax}$ by 60 milliseconds or less, that is, if $T_{zc3rd-+} \leq T_{max}+60$ msec, or if $T_{zc3rd-+}$ is later than 300 milliseconds after systolic onset, that is, if $T_{zc3rd-+} > T_{so}+300$ msec the system determines that the second shoulder cannot be located (steps 35-35A). Otherwise, the system takes the pulse point corresponding to Zc3rd-+ as the second shoulder point, which is the point associated with the return of the secondary, or reflected, wave from the lower body (step 35B). If the pulse is a Type A pulse, the processor equates the first shoulder with the pulse point which corresponds to the MAX3rd point of curve 19 (step 36) and the second shoulder with the SMAX point (step 37), as shown in FIG. 18.

Using a second alternative process, as set forth in FIG. 20, the processor takes the third derivative of the pulse (curve 19 in FIGS. 16-18) locates the Zc3rd+- point, which is the first positive-to-negative zero crossing point of the third derivative which succeeds the MAXdpdt point, and finds its time of occurrence, $T_{zc3rd+-}$ (step 38). The processor then locates the point of zero crossing of the third derivative from negative-to-positive immediately following the Zc3rd+- point, that is, Zc3rd-+ and its time of occurrence, $T_{zc3rd-+}$ (point 22 in FIGS. 16-18), (step 38). Next, the processor determines whether the SMAX point follows Zc3rd+- by at least 60 milliseconds, that is, if $T_{smax} \geq T_{zc3rd+-}+60$ msec (step 40). If so, the processor determines that the pulse is a Type A pulse, as shown in FIGS. 1 and 18 (steps 40-42A). Otherwise, the processor determines that the pulse has a shape which is associated with an younger subject and, thus, is a Type B or C pulse, as shown in FIGS. 1 and 16-17 (steps 40-42B).

If the pulse is Type B or C, the processor equates first shoulder point, which is the point associated with the peak of the primary pressure wave, with the SMAX point (step 44). The processor then compares $T_{zc3rd-+}$ with $T_{smax}$. If $T_{zc3rd-+}$ is within 60 milliseconds of $T_{smax}$, or it is later than 300 milliseconds after systolic onset, the system determines that the second shoulder cannot be located (steps 45-45A). Otherwise, the system takes the pulse point corresponding to the Zc3rd-+ point as the second shoulder point, (step 45B). If the pulse is a Type A pulse, the processor equates the first shoulder with the pulse point which corresponds to the Zc3rd+- point (point 20 of curve 19), and the second shoulder with the SMAX point (steps 46-47) as shown in FIG. 18.

Presently the system is configured to use one of these two alternatives. However, it is expected that the system will eventually use a combination of these alternatives to determine pulse type and shoulder location.

The accuracy of this analysis may be queried under the following two circumstances:

1-) When the time from the wave foot to the first systolic shoulder ($T_{so}$ to $T_{max3rd}$) or ($T_{so}$ to $T_{zc3rd-+}$) is less than 80 milliseconds; and 2-) When the MAXdpdt point associated with the recorded peripheral wave is less than 300 mmHg/sec.

The first circumstance indicates that the patient may have aortic valve disease or may have had a prosthetic aortic valve. In either case, the first shoulder tends to be low on the pressure wave, and thus, augmentation may be over estimated. The second circumstance indicates that the patient may have an obstruction between the heart and the arterial pulse recording site—either a localized obstruction or a generalized spasm. In this case, the transfer function may not accurately portray the pressure pulses in the ascending aorta. Accordingly, if either of these circumstances is present, the processor "flags" the results to indicate to a user that the results may be overstated or not entirely accurate.

4. Estimation of Augmentation Index and Central Aortic Peak Pressure from the Measured Peripheral Pulse Referring now to FIG. 21, once the first and second shoulders of the pulse are identified (steps 90-96), the processor determines if the pulse has an augmented peak. Using the peripheral pulse, the system first generates a Reverse Shoulder Index ("RSI") by dividing (i) the pressure at the second shoulder, $P_{s2}$, minus the pressure at systolic onset, $P_{s0}$, by (ii) the pressure at the first shoulder, $P_{s1}$, minus $P_{s0}$ (steps 98-100). The RSI is expressed as a percentage, and thus, the quotient is multiplied by 100.

If the RSI is less than an emperically predetermined minimum value, 9% for radial or 38% for brachial in the preferred embodiment, it indicates that the pulse is associated with non-augmented aortic pressure (steps 102 and 102a). If the RSI is greater than the appropriate predetermined minimum value, the pulse is associated with augmented aortic pressure.

Figure 22:
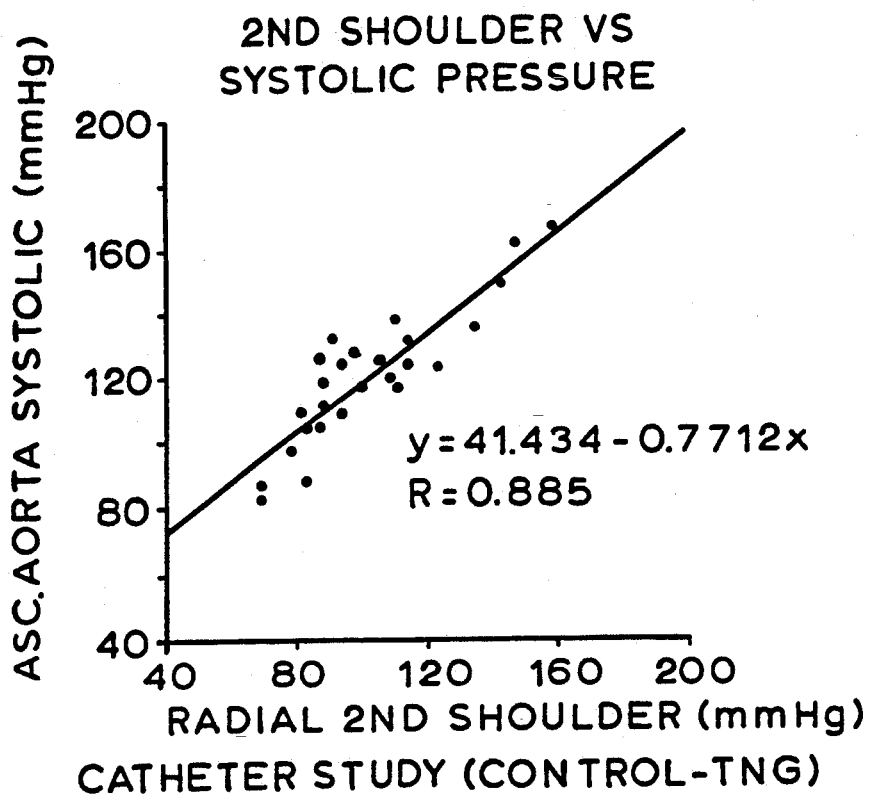
FIGS. 22 and 22a are graphs of the distribution of aortic systolic pressure as a function of radial artery second shoulder pressure and of brachial artery second shoulder pressure, respectively.
Figure 22A:
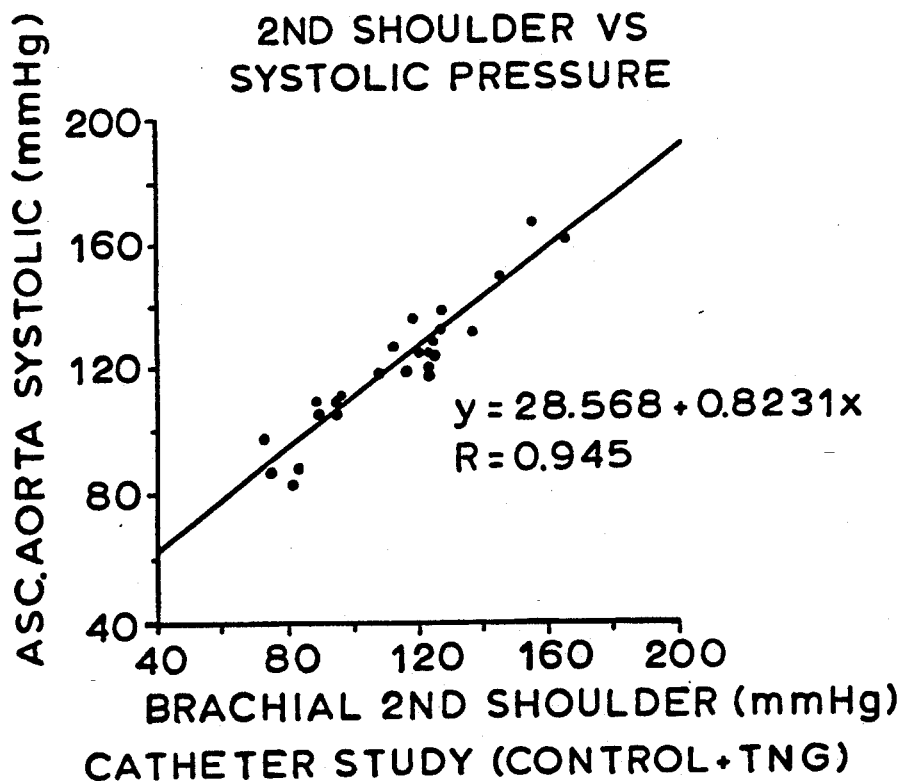

If the RSI value indicates that the pulse is not associated with augmented central pressure, the processor next calculates central pressure, CP, by substituting the pressure associated with the second shoulder, $P_{s2}$, into the appropriate formula (steps 106 and 106a):

$$CP = 41.3 + 0.77 * P_{s2} \text{ (mm Hg)} \quad (1) \text{ From the radial pulse}$$

$$CP = 28.6 + 0.82 * P_{s2} \text{ (mm Hg)} \quad (1a) \text{ From the brachial pulse}$$

where "*" indicates multiplication and the numerals 41.3 and 0.77 are the y-intercept and the slope, respectively, of a line corresponding to the best estimate of data presented in a graph of aortic systolic pressure versus radial artery second shoulder pressure as shown in FIG. 22, and the numerals 28.6 and 0.82 are the y-intercept and slope, respectively, of a line corresponding to the best estimate of data presented in a graph of aortic systolic pressure versus brachial artery second shoulder pressure as shown in FIG. 22a.

The data in FIG. 22 and 22a were collected invasively from a number of patients and the values in formulas 1 and 1a represent best estimates of the data. These values may change as more data become available. Similarly, the values of the minimum RSI's associated with augmentation were determined from invasively collected data. These values may change, also, as more data become available.

Figure 23A:
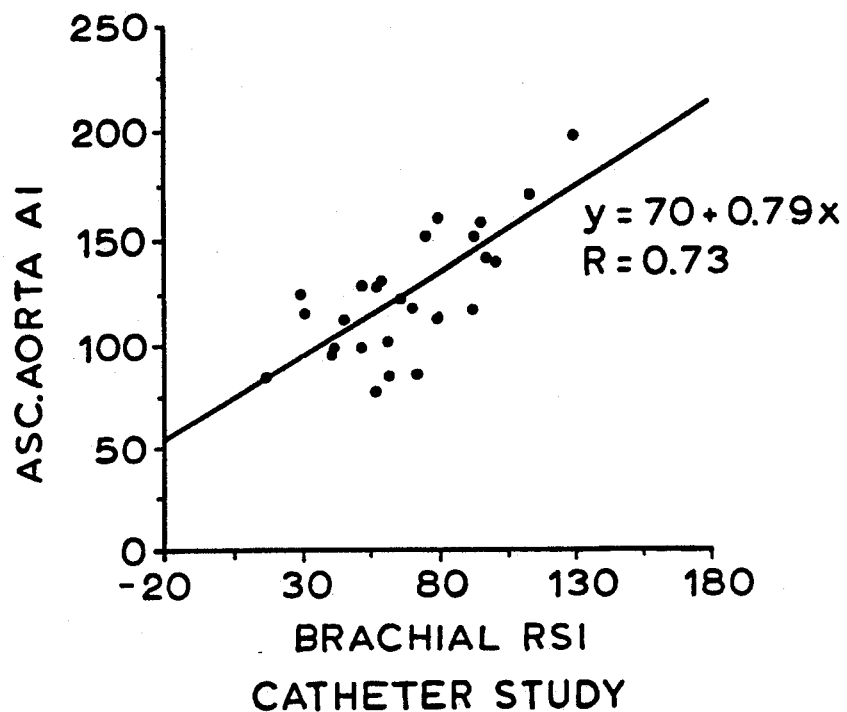
FIGS. 23 and 23a are graphs of the distribution of augmentation indices associated with aortic pressure as a function of the augmentation indices associated with radial pressure and with brachial pressure, respectively.
Figure 23:
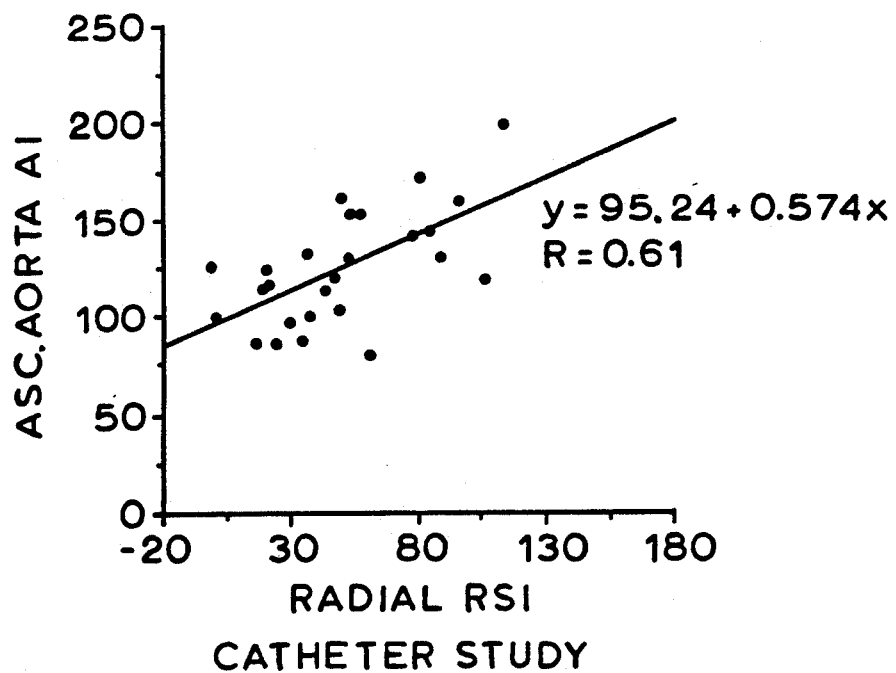

If the RSI value indicates that the pulse is associated with augmented central aortic pressure, the processor generates an augmentation index, AI. The AI corresponds to a comparison of the amplitude of the secondary wave to the amplitude of the primary wave. If AI exceeds "100%" it indicates that the secondary wave exceeds the primary wave, and thus, that early wave reflection is boosting aortic and left ventricular peak pressure. To calculate the AI, as a percentage, the processor substitutes the appropriate RSI value into one of the following formulas (steps 104 and 104a):

$$AI = 95 + 0.57 * RSI \quad (2) \text{ From Radial}$$

$$AI = 70 + 0.79 * RSI \quad (2a) \text{ From Brachial}$$

where "*" indicates multiplication and the numerals 95 and 70, and 0.57 and 0.79 are the y-intercepts and the slopes, respectively, of lines corresponding to the best estimates of data presented in graphs of augmentation indices of the aortic pressure versus radial artery and aortic pressure versus brachial artery pressure, as shown in FIGS. 23 and 23a, respectively. The data for FIGS. 23 and 23a were calculated from pressures measured invasively in a number of patients. The values in formulas (2) and/or (2a) may change as more data become available.

Figure 21:
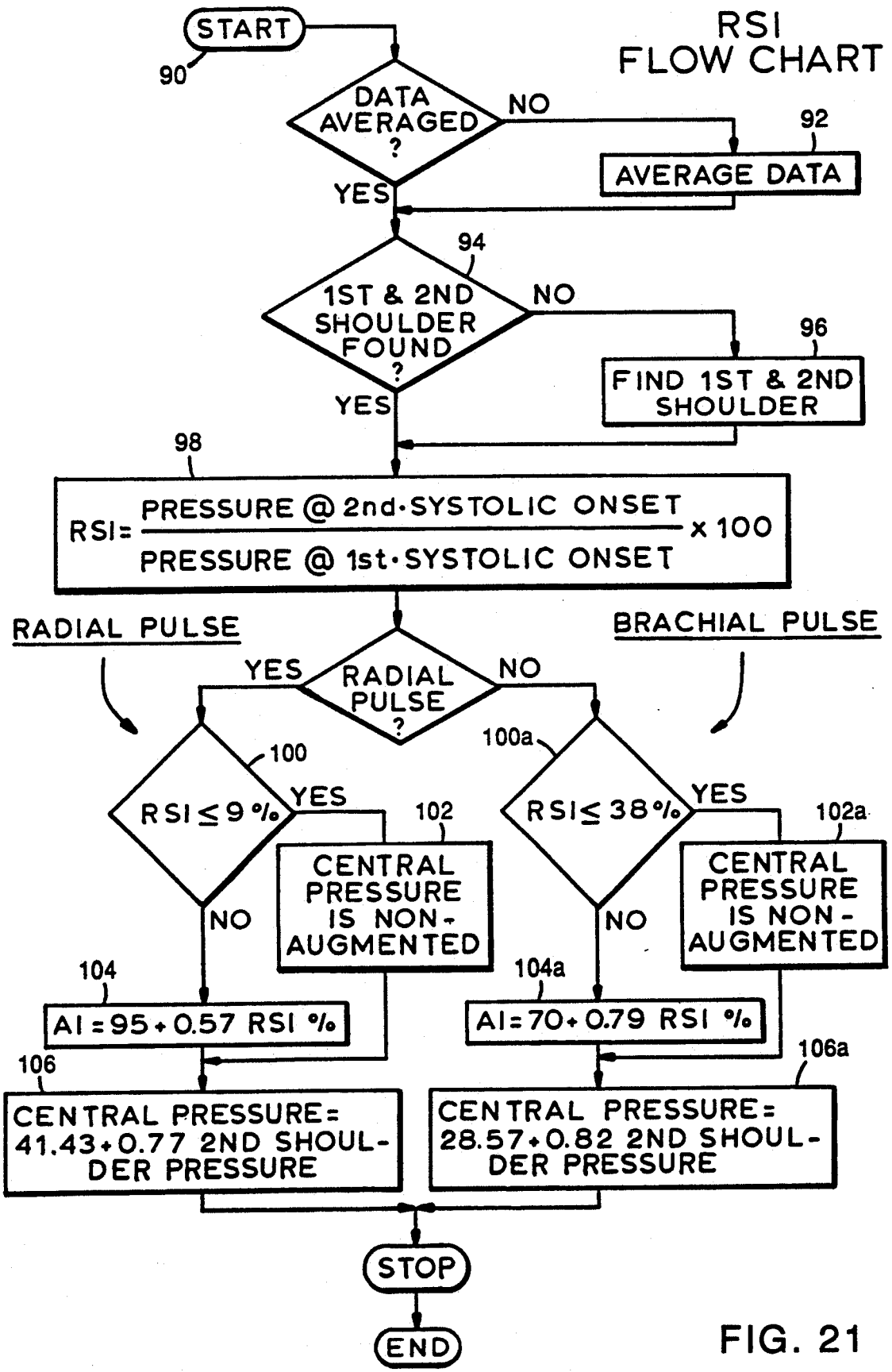
FIG. 21 is a flow chart for determining the central aortic pressure from the peripheral pressure pulse.

The processor then calculates the central pressure corresponding to the augmented pulse using formula (1) or (1a) as appropriate. The central pressure can be similarly calculated from the pressure in the brachial artery. The differences between such a calculation and the calculation depicted in FIG. 21 are the y-intercepts and slopes of the central pressure and augmentation index formulas which can be calculated from invasively measured data.

5. Determination of Systolic and Diastolic Pressure and Augmentation Index from the Synthesized Pressure Pulse Using the synthesized pulse and the calculated time of the occurrence of the wave foot and the incisura, the system may determine maximum and mean systolic and mean diastolic pressures and various pressure-related indices, as well a the augmentation index. The system thus first determines from the pulse the maximum systolic and diastolic pressures and calculates the respective mean pressures. It then calculates a systolic pressure-time index (SPTI), which is mean systolic pressure multiplied by the length of time in systole, multiplied, also, by the heart rate, and a diastolic pressure-time index (DPTI), which is the mean diastolic pressure multiplied by the length of time in diastole and the heart rate. Using these indices, the system calculates a subendocardial viability ratio, which is DPTI÷SPTI.

Figure 24:
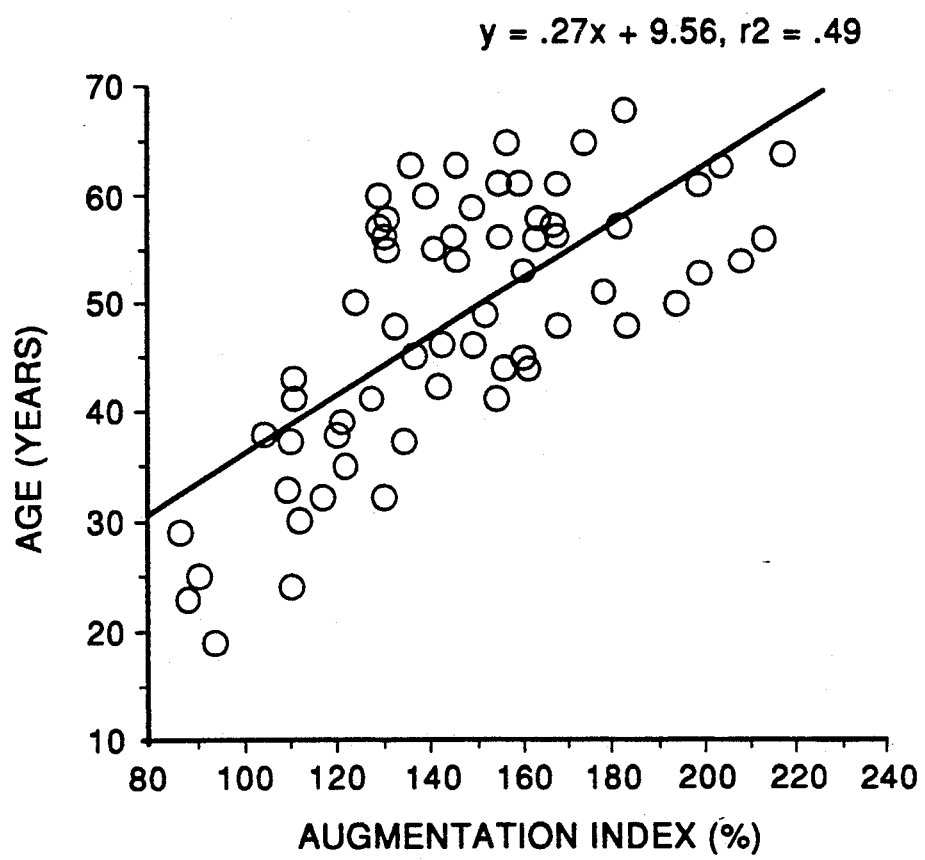
FIG. 24 is a graph of the correspondence between augmentation indices and age for the ascending aorta.

The system, also, determines whether there is augmentation and, if necessary, an augmentation index by first calculating if $P_{s2}-P_{s1}$ is positive. If it is, the pressure is augmented, augmentation is $P_{s2}-P_{s1}$ (mm Hg), and the augmentation index $(P_{s2}-P_{s0})\div(P_{s1}-P_{s0})$ is greater than 100%. The system then compares this augmentation index and/or the augmentation index calculated using the peripheral pulse with the chart of augmentation indices versus age (FIG. 24 per the ascending aorta) to determine for the patient a "reference age." This reference age relates the condition of the patient with the condition of a "reference" patient who does not have heart or artery diseases.

6. Summary and Clinical Relevance

The various indices, and in particular, the SPTI and DPTI, are important in determining both myocardial oxygen demand, which depends on the pressure developed in systole, and myocardial oxygen supply, which depends on the pressure maintained in the aorta during diastole. Before the current invention, such indices were calculated based on pressures measured in the aorta through invasive procedures.

The SPTI, DPTI, augmentation index absolute augmentation (in mm Hg) and reference age, are useful in diagnosing, treating and monitoring patients with angina pectoris, cardiac failure and hypertension, and all are generated by the current system without invasion of the aorta. Thus a doctor may monitor noninvasively the effects of medication, exercise, et cetera, on the systolic and diastolic blood pressure in the ascending aorta and pressure in the left ventricle of the heart during systole in order to gauge appropriately the effects of the medication or treatment.

At present a physician assumes that the pressure recorded in an upper limb artery is identical to that in the ascending aorta and in the left ventricle during systole. In other words, a physician assumes that the modulus of the transfer function remains at unity for all frequencies. Such an assumption can be highly erroneous, especially during exercise, in shock states, cardiac failure, and during treatment with vasodilator agents. The new system adds far greater precision to the determination of left ventricular load and enables better treatment of patients with hypertension, angina pectoris, and heart failure, and more accurate monitoring of patients in intensive care situations than do prior systems. And, the new system does this using pressure recorded in an upper limb peripheral artery.

Before the current invention, physicians could not accurately monitor left ventricular load and aortic pressures from peripheral pressure, whether the peripheral pressure was recorded non-invasively, or, indeed invasively. For accurate determination of central aortic pressure, a catheter had to be placed and maintained in the central aorta. This central aortic cannulation entails substantial risk of clot formation and embolization to vital organs, including the brain (with risk of stroke), the heart (with risk of myocardial infarction) and the kidneys (with risk of kidney failure). However, with the current invention such risks can be avoided.

Also, before the current invention, physicians recording peripheral pressures only were likely to overestimate increases in aortic and left ventricular pressure by up to 80 mmHg, underestimate the degree of reduction in aortic systolic pressure during shock by up to 20 mmHg, and/or underestimate the degree of reduction in the left ventricular load induced by vasodilator therapy by up to 20 mmHg. With the current invention, the physician can accurately monitor left ventricular systolic load and central aortic pressure in patients under various conditions, such as shock or undergoing vasodilator therapy without the hazards of aortic cannulation discussed above. Accordingly, he can better plan therapies and monitor drug action, and better choose between different types of drugs for patients in these various conditions.

The foregoing description has been limited to a number of specific embodiments of this invention. It will be apparent, however, that variations and modifications may be made to the invention, with the attainment of some or all of the advantages of the invention. Therefore, it is the object of the appended claims to cover all such variations and modifications as come within the true spirit and scope of the invention.

What is claimed as new and desired to be secured by Letters Patent of the United States is:

1. A method of determining systolic and diastolic pressure in the ascending aorta from measurements of pressure in an upper body peripheral artery, said method comprising the steps of:
   A. measuring pressure pulses in a peripheral artery and producing an electrical signal representing the pressure pulses;
   B. deriving a Fourier transform for the measured peripheral pulses;
   C. dividing the peripheral pulse Fourier transform by a transfer function H(w) relating a Fourier transform of pressure pulses in the peripheral artery and a Fourier transform of pressure pulses in the aorta, thereby producing a Fourier transform associated with the aortic pressure pulse;
   D. deriving the inverse of the Fourier transform associated with the aortic pressure pulse, thereby producing an electrical signal representing a synthesized ascending aortic pressure pulse;
   E. determining in the signal representing the measured peripheral pulse a point of systolic onset by taking a first derivative of the measured peripheral pulse and locating a zero crossing from negative-to-positive which precedes a maximum point on the first derivative curve;
   F. determining the location of a point of incisura in the signal representing the measured peripheral pressure pulse by finding in a signal representing the third derivative of the measured peripheral pulse a zero crossing from positive-to-negative in proximity to the largest maximum point of the third derivative after the peak of a second systolic shoulder;
   G. determining in the electrical signal representing the synthesized aortic pressure pulse, the systole and diastole components of the synthesized signal based on the location of the incisura and systolic onset in the signal representing the measured peripheral pulse;
   H. determining from the electrical signal representing the synthesized aortic pressure pulse a maximum systolic pressure and a maximum diastolic pressure; and
   I. displaying a graph of the electrical signal representing the measured peripheral pulse, the electrical signal representing the synthesized ascending aortic pressure pulse and the related maximum systolic and diastolic pressures.

2. The method of claim 1, wherein the method further includes the steps of:

J. determining, from the electrical signal representing the synthesized ascending aortic pressure pulse, mean aortic systolic pressure;

K. measuring heart rate; and

L. calculating a systole pressure-time index based on the mean systolic pressure determined from the maximum systolic pressure determined in step H, the length of time in systole calculated from systolic onset to the point of incisura as determined in step G and the measured heart rate determined in step K; and M. displaying the systole pressure-time index.

3. The method of claim 2, wherein the method further includes the steps of:

N. determining from the electrical signal representing the synthesized aortic pressure pulse, mean aortic pressure during diastole;

O. calculating a diastole pressure-time index based on the mean aortic diastolic pressure during diastole determined from the maximum systolic pressure determined in step H, the length of time in diastole determined in step G and the measured heart rate determined in step K; and P. displaying the diastole pressure-time index.

4. The method of claim 3, wherein the method further includes the step of determining subendocardial viability ratio by dividing the diastolic pressure-time index by the systolic pressure-time index.

5. The method of claim 1, wherein the step of separating the electrical signal representing the synthesized aortic pressure pulse into systole and diastole components further includes:

i. determining the duration of systole by calculating the time difference between the occurrence of systolic onset and the occurrence of the incisura in the peripheral pressure pulse; and ii. identifying the incisura in the electrical signal representing the synthesized aortic pressure pulse as a point separated by the time interval determined in step i from a point on the synthesized aortic pressure pulse corresponding to systolic onset.

6. A method of claim 1, wherein the step of locating the incisura in the signal representing the measured peripheral pressure pulse further includes locating a zero crossing from positive-to-negative associated with the largest maximum in the third derivative after a point corresponding to a first systolic shoulder, if the second systolic shoulder cannot be identified.

7. The method of claim 1, wherein the step of locating the incisura further includes:

i. locating in the signal representing the measured peripheral pressure pulse a maximum pressure point, SMAX, and determining its time of occurrence, $T_{SMAX}$;

ii. locating in a first derivative of the signal representing the measured peripheral pressure pulse a maximum point, MAXdpdt;

iii. locating in a third derivative of the signal representing the measured peripheral pressure pulse a maximum point, Max3rd, which immediately follows a point on the third derivative which corresponds to MAXdpdt and determining its time of occurrence, $T_{max3rd}$;

iv. if $T_{smax}$ is not greater than or equal to $T_{max3rd}+60$ msec, identifying SMAX as the peak of a first systolic shoulder and identifying a next negative-to-positive zero crossing point Zc3rd-+ of the third derivative as the point which corresponds to the peak of a second systolic shoulder of the signal representing the measured peripheral pressure pulse providing that $T_{zc3rd-+}$ is less than $T_{SMAX}+60$ msec or and is greater than 300 msec after systolic onset; and v. if $T_{smax}$ follows $T_{max3rd}$ by 60 msec or more, identifying the Max3rd point as corresponding to the peak of the first systolic shoulder of the signal representing the measured peripheral pressure pulse and identifying SMAX as the peak of the second systolic shoulder.

8. The method of claim 1, wherein the step of locating the incisura further includes:

i. locating in the measured peripheral pressure pulse a maximum pressure point, SMAX, and determining its time of occurrence, $T_{SMAX}$;

ii. locating in a first derivative of the signal representing the measured peripheral pressure pulse a maximum point, MAXdpdt and determining its time of occurrence, $T_{MAXdpdt}$.

iii. locating in a third derivative of the signal representing the measured peripheral pressure pulse a first positive-to-negative zero crossing point, Zc3rd+-, which immediately follows $T_{maxdpdt}$ and determining its time of occurrence $T_{zc3rd+-}$;

iv. If $T_{smax}$ is not greater than or equal to $T_{zc3rd+-}+60$ msec, identifying SMAX as corresponding to the peak of a first systolic shoulder and identifying a point on the signal representing the measured peripheral pressure pulse corresponding to a next negative-to-positive zero crossing point, Zc3rd-+, as the peak of a second systolic shoulder providing that $T_{zc3rd-+}$ is less than 60 msec + $T_{smax}$ or greater than 300 msec from systolic onset; and v. $T_{smax}$ follows $T_{zc3rd+-}$ by 60 msec or more, identifying a point on the signal representing the measured peripheral pressure pulse which corresponds to the Zc3rd+- point as the peak of the first systolic shoulder and identifying SMAX as the peak of the second systolic shoulder.

9. The method of claim 1, wherein the step of separating the signal representing the synthesized aortic pressure pulse into systole and diastole components includes:

i. locating in the signal representing the synthesized aortic pressure pulse a maximum pressure point, SMAX and determining its time of occurrence, $T_{SMAX}$;

ii. locating in a first derivative of the signal representing the synthesized aortic pressure pulse a maximum point, MAXdpdt;

iii. locating in a third derivative of the signal representing the synthesized aortic pressure pulse a maximum point, Max3rd, which immediately follows a point on the third derivative which corresponds to MAXdpdt and determining its time of occurrence, $T_{max3rd}$;

iv. if $T_{smax}$ is not greater than or equal to $T_{max3rd}+60$ msec, identifying SMAX as the peak of a first systolic shoulder and identifying a next negative-to-positive zero crossing point Zc3rd-+ of the third derivative as the point which corresponds to the peak of a second systolic shoulder of the signal representing the synthesized aortic pressure pulse providing that $T_{zc3rd-+}$ is less than 60 msec+$T_{smax}$ or greater than 300 msec from systolic onset; and v. if $T_{smax}$ follows $T_{max3rd}$ by 60 msec or msec, identifying the Max3rd point as corresponding to the peak of the first systolic shoulder of the synthesized pulse and identifying SMAX as the peak of the second systolic shoulder.

10. The method of claim 9, wherein the method further includes the steps of:
   A. determining if the signal representing the synthesized aortic pressure pulse corresponds to an augmented ascending aorta pressure pulse by determining if the pressure peak at the second
   ii. locating in a first derivative of the signal representing the measured peripheral pressure pulse a maximum point, MAXdpdt;
   iii. locating in a third derivative of the signal representing the measured peripheral pressure pulse a maximum point, Max3rd, which immediately follows a point on the third derivative which corresponds to MAXdpdt and determining its time of occurrence, $T_{MAX3rd}$;
   iv. If $T_{SMAX}$ is not greater than or equal to $T_{max3rd}+60$ msec, identifying SMAX as the peak of a first systolic shoulder and identifying a next negative-to-positive zero crossing point Zc3rd-+ of the third derivative as the point which corresponds to the peak of a second systolic shoulder of the signal representing the measured peripheral pressure pulse providing that $T_{zc3rd-+}$ follows is less than $T_{SMAX}+60$ msec or greater than 300 msec from systolic onset; and
   v. if $T_{SMAX}$ follows $T_{MAX3rd}$ by 60 msec or more, identifying the Max3rd point as corresponding to the peak of the first systolic shoulder of the signal representing the synthesized aortic pressure pulse and identifying SMAX as the peak of the second systolic shoulder.

11. The method of claim 10, wherein the method further includes step of determining a reference age corresponding to the augmentation index, wherein the reference age categorizes the functional age of the arterial tree.

12. The method of claim 1, wherein the step of separating the signal representing the synthesized aortic pressure pulse into systole and diastole components includes:
   i. locating in the signal representing the aortic pressure pulse a maximum pressure point, SMAX and determining its time of occurrence, $T_{SMAX}$;
   ii. locating in a first derivative of the signal representing the synthesized aortic pressure pulse a maximum point, MAXdpdt and determining its time of occurrence, $T_{MAXdpdt}$;
   iii. locating in a third derivative of the signal representing the synthesized aortic pressure pulse a positive-to-negative zero crossing point, Zc3rd+-, which immediately follows $T_{maxdpdt}$ and determining its time of occurrence $T_{zc3rd+-}$;
   iv. if $T_{SMAX}$ is not greater than or equal to $T_{zc3rd+-}+60$ msec identifying SMAX as corresponding to the peak of a first systolic shoulder and identifying a point on the signal representing the synthesized aortic pressure pulse corresponding to a next negative-to-positive zero crossing point, Zc3rd-+, as the peak of a second systolic shoulder providing that $T_{zc3rd-+}$ is less than 60 msec from $T_{smax}$ or greater than 300 msec+systolic onset; and
   v. if $T_{smax}$ follows $T_{zc3rd+-}$ by 60 msec or more, identifying a point of the signal representing the synthesized aortic pressure pulse which corresponds to the Zc3rd+- point as the peak of the first systolic shoulder and identifying SMAX as the peak of the second systolic shoulder.

13. The method of claim 1, wherein the method further includes the step of determining the pressure at the end of systole based on the pressure at the point on the synthesized aortic pressure pulse at which systole ends.

14. The method of claim 1, wherein the step of locating the incisura further includes:
   i. locating in the signal representing the synthesized aortic pressure pulse a maximum pressure point, SMAX, and determining its time of occurrence, $T_{SMAX}$;
   ii. locating in a first derivative of the signal representing the measured peripheral pressure pulse a maximum point, MAXdpdt;
   iii. locating in a third derivative of the signal representing the measured peripheral pressure pulse a maximum point, Max3rd, which immediately follows a point on the third derivative which corresponds to MAXdpdt and determining its time of occurrence, $T_{MAX3rd}$;
   iv. if $T_{SMAX}$ is not greater than or equal to $T_{max3rd}+60$ msec, identifying SMAX as the peak of a first systolic shoulder and identifying a next negative-to-positive zero crossing point Zc3rd-+ of the third derivative as the point which corresponds to the peak of a second systolic shoulder of the signal representing the measured peripheral pressure pulse providing that $T_{zc3rd-+}$ follows is less than $T_{SMAX}+60$ msec or greater than 300 msec from systolic onset; and
   v. if $T_{SMAX}$ follows $T_{MAX3rd}$ by 60 msec or more, identifying the Max3rd point as corresponding to the peak of the first systolic shoulder of the signal representing the synthesized aortic pressure pulse and identifying SMAX as the peak of the second systolic shoulder.

15. A method of determining pressure in the ascending aorta from measurements of pressure in an upper body peripheral artery, said method comprising the steps of:
   A. non-invasively measuring pressure pulses in a peripheral artery and producing an electrical signal representing the pressure;
   B. deriving a Fourier transform for the measured peripheral pulses;
   C. dividing the peripheral pulse Fourier transform by a transform function H(w) relating a Fourier transform of pressure pulses in the peripheral artery and a Fourier transform of pressure pulses in the aorta, thereby producing a Fourier transform associated with the aortic pressure pulse;
   D. deriving the inverse of the Fourier transform associated with the aortic pressure pulse, thereby producing an electrical signal representing a synthesized ascending aortic pressure pulse;
   E. determining in the signal representing the measured peripheral pulse a point of systolic onset by taking a first derivative of the measured peripheral pulse and locating a zero crossing from negative-to-positive which precedes a maximum point on the first derivative curve;

F. determining the location of a point of incisura in the signal representing the measured peripheral pressure pulse by finding in a signal representing the third derivative of the measured peripheral pulse a zero crossing from positive-to-negative in proximity to the largest maximum point of the third derivative after the peak of a second systolic shoulder;

G. separating in the electrical signal representing the synthesized aortic pressure pulse, the systole and diastole components of the synthesized signal based on the location of the incisura and systolic onset in the signal representing the measured peripheral pulse;

H. determining from the electrical signal representing the synthesized aortic pressure pulse a maximum systolic pressure and a maximum diastolic pressure; and I. displaying a graph of the electrical signal representing the measured peripheral pulse, the electrical signal representing the synthesized ascending aortic pressure pulse and the related maximum systolic and diastolic pressures.

16. The method of claim 15, wherein the method further includes the steps of:

J. determining, from the electrical signal representing the synthesized ascending aortic pressure pulse, mean aortic systolic pressure;

K. measuring heart rate; and

L. calculating a systole pressure-time index based on the mean systolic pressure determined from the maximum systolic pressure determined in step H, the length of time in systole calculated from systolic onset to the point of incisura as determined in step G and the measured heart rate determined in step K; and M. displaying the systole pressure-time index.

17. The method of claim 16, wherein the method further includes the steps of:

N. determining from the electrical signal representing the synthesized aortic pressure pulse, mean aortic pressure during diastole.;

O. calculating a diastole pressure-time index based on the mean aortic diastolic pressure during diastole determined from the maximum systolic pressure determined in step H, the length of time in diastole determined in step G and the measured heart rate determined in step J; and P. displaying the diastole pressure-time index.

18. The method of claim 17, wherein the method further includes the step of determining subendocardial viability ratio by dividing the diastolic pressure-time index by the systolic pressure-time index.

19. The method of claim 15, wherein the step of separating the electrical signal representing the synthesized aortic pressure pulse into systole and diastole components further includes i. determining the duration of systole by calculating the time difference between the occurrence of systolic onset and the occurrence of the incisura in the peripheral pressure pulse; and ii. identifying the incisura in the electrical signal representing the synthesized aortic pressure pulse as a point separated by the time interval determined in step from a point on the synthesized aortic pressure pulse which corresponds to systolic onset.

20. The method of claim 15, wherein the method further includes the step of determining the pressure at the end of systole based on the pressure at the point on the synthesized aortic pressure pulse at which systole ends.

21. The method of claim 15, wherein the step of non-invasively measuring the peripheral pressure includes use of a tonometer.

22. A method of determining pressure in the ascending aorta from measurements of pressure in an upper body peripheral artery, said method comprising the steps of:

A. non-invasively measuring pressure pulses in a peripheral artery and producing an electrical signal representing the pressure;

B. manipulating the signal to produce a signal representing a synthesized aortic pressure pulse;

C. determining in the signal representing the measured peripheral pulse a point of systolic onset by taking a first derivative of the measured peripheral pulse and locating a zero crossing from negative-to-positive which precedes a maximum point on the first derivative curve;

D. determining the location of a point of incisura in the signal representing the measured peripheral pressure pulse by finding in a signal representing the third derivative of the measured peripheral pulse a zero crossing from positive-to-negative in proximity to the largest maximum point of the third derivative after the peak of a second systolic shoulder;

E. separating in the electrical signal representing the synthesized aortic pressure pulse, the systole and diastole components of the synthesized signal based on the location of the incisura and systolic onset in the signal representing the measured peripheral pulse;

F. determining from the electrical signal representing the synthesized aortic pressure pulse a maximum systolic pressure and a maximum diastolic pressure; and G. displaying a graph of the electrical signal representing the measured peripheral pulse, the electrical signal representing the synthesized ascending aortic pressure pulse and the related maximum systolic and diastolic pressures.

23. The method of claim 22, wherein the method further includes the steps of:

H. determining, from the electrical signal representing the synthesized ascending aortic pressure pulse, mean aortic systolic pressure;

I. measuring heart rate; and

J. calculating a systole pressure-time index based on the mean systolic pressure determined from the maximum systolic pressure determined in step F, the length of time in systole calculated from systolic onset to the point of incisura as determined in step G and the measured heart rate determined in step J; and K. displaying the systole pressure-time index.

24. The method of claim 23, wherein the method further includes the steps of:

L. determining from the electrical signal representing the synthesized aortic pressure pulse, mean aortic pressure during diastole;

M. calculating a diastole pressure-time index based on the mean aortic diastolic pressure during diastole determined from the maximum systolic pressure determined in step F, the length of time in diastole determined in step G and the measured heart rate determined in step I; and N. displaying the diastole pressure-time index.

25. The method of claim 22, wherein the step of separating the electrical signal representing the synthesized aortic pressure pulse into systole and diastole components further includes i. determining the duration of systole by calculating the time difference between the occurrence of systolic onset and the occurrence of the incisura in the peripheral pressure pulse; and ii. identifying the incisura in the electrical signal representing the synthesized aortic pressure pulse as a point separated by the time interval determined in step i from a point on the pulse corresponding to systolic onset.

* * * * *

UNITED STATES PATENT AND TRADEMARK OFFICE
CERTIFICATE OF CORRECTION

PATENT NO. : 5,265,011
DATED : November 23, 1993
INVENTOR(S) : Michael F. O'Rourke It is certified that error appears in the above-indentified patent and that said Letters Patent is hereby corrected as shown below:

In claim 10, column 17, line 14, after "second" insert

--systolic shoulder is greater than the pressure peak at the first systolic shoulder; and B. determining augmentation as $P_{s2}-P_{s1}$ in mm Hg, and C. determining the augmentation index as $(P_{s2} - P_{s0}) \div (P_{s1} - P_{s0})$, where $P_{s2}$ is the pressure associated with the second shoulder and $P_{s0}$ is the pressure at systolic onset.--

Also in claim 10, column 17, lines 15-40, delete steps ii-v in their entirety.

In claim 12, column 18, line 4, delete "of" and insert --on--.

UNITED STATES PATENT AND TRADEMARK OFFICE
CERTIFICATE OF CORRECTION

PATENT NO. : 5,265,011
DATED : November 23, 1993
INVENTOR(S) : Michael F. O' Rourke It is certified that error appears in the above-indentified patent and that said Letters Patent is hereby corrected as shown below:

In claim 19, column 19, line 65, after "step" insert --i--.

Signed and Sealed this

Second Day of August, 1994

BRUCE LEHMAN

Attest:

Attesting Officer

Commissioner of Patents and Trademarks